(12) United States Patent
Kitamura et al.

(10) Patent No.: US 7,459,268 B2
(45) Date of Patent: Dec. 2, 2008

(54) METHOD FOR SCREENING AGENT ACTING ON CELL WALL

(75) Inventors: Akihiro Kitamura, Ichikawa (JP); Ryohei Nakajima, Ichikawa (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 239 days.

(21) Appl. No.: 10/492,202

(22) PCT Filed: Oct. 22, 2002

(86) PCT No.: PCT/JP02/10932

§ 371 (c)(1), (2), (4) Date: Nov. 17, 2004

(87) PCT Pub. No.: WO03/035898

PCT Pub. Date: May 1, 2003

(65) Prior Publication Data
US 2005/0069965 A1 Mar. 31, 2005

(30) Foreign Application Priority Data
Oct. 22, 2001 (JP) ............................. 2001-323293

(51) Int. Cl.
*C12Q 1/00* (2006.01)
(52) U.S. Cl. ......................................................... 435/4
(58) Field of Classification Search ........................ None
See application file for complete search history.

(56) References Cited

U.S. PATENT DOCUMENTS

| 6,027,910 | A | 2/2000 | Klis et al. |
| 2004/0091949 | A1 | 5/2004 | Kitamura et al. |
| 2005/0069965 | A1 | 3/2005 | Kitamura et al. |

FOREIGN PATENT DOCUMENTS

| EP | 0916726 | 5/1999 |
| EP | 1283261 | 2/2003 |
| JP | 7-508652 | 9/1995 |
| JP | 9-56384 | 3/1997 |
| JP | 2000-102387 | 4/2000 |
| WO | 94/01567 | 1/1994 |
| WO | 99/67419 | 12/1999 |
| WO | 01/83733 | 11/2001 |
| WO | 03/035898 | 5/2003 |

OTHER PUBLICATIONS

Hamada et al. Mol Gen Genet 1998;258:53-59.*
Brul et al. Food technol. biotechnol. 1997;35(4):267-274.*
M.A. Ferguson et al., Ann. Rev. Biochem., vol. 57, pp. 285-320, 1988.
C.F. Lu et al., Mol. Cell Biol., vol. 14, pp. 4825-4833, 1994.
R. Kollar et al., J. Biol. Chem., vol. 272, pp. 17762-17775, 1997.
K. Hamada et al., Mol. Gen. Genet., vol. 258, pp. 53-59, 1998.
L. Caro, Yeast, vol. 13, pp. 1477-1489, 1997.
J.M.V.D. Vaart et al., Appl. Environ. Microbiol., vol. 63, pp. 615-620, 1997.
T. Murai et al., Appl. Environ. Microbiol., vol. 63, pp. 1362-1366, 1997.
C.F. Lu et al., J. Cell. Biol., vol. 128, pp. 333-340, 1995.
The Pharmaceutical Society of Japan, The 120th Annual Meeting, Abstracts 2, p. 153, Lecture No. 30 [PB]15-71, 2000.
B.P. Cormack et al., Gene, vol. 173, pp. 33-38, 1996.
H. Horiuchi et al., Agric. Biol. Chem., vol. 54, pp. 1771-1779, 1990.
J.M. Varrt et al., J. Bacteriol., vol. 177, pp. 3104-3110, 1995.
P.L. Liljestrom, Nucl. Acids Res., vol. 13, pp. 7257-7268, 1985.
R. Taussig et al., Nucl. Acids Res., vol. 11, pp. 1943-1954, 1983.
M. Vai et al., J. Biol. Chem., vol. 266, pp. 12242-12248, 1991.
H. Turakainen et al., Appl. Environ. Microbiol., vol. 59, pp. 2622-2630, 1993.
M.P. Schreuder et al., Yeast, vol. 9, pp. 399-409, 1993.
J.P. Gaughran et al., J. Bacteriol., vol. 176, pp. 5857-5860, 1994.
English Language Abstract of JP 9-56384.
Shahinlan, S. et al., Beta-1, 6-glucan synthesis in *Saccharomyces cerevisiae*, Molecular Biology, vol. 35(3), pp. 477-489 (2000).
Lu, Cha-Fen et al., Glycosyl phosphatidylinositol-dependent cross-linking of alpha-agglutinin and beta-1,6,-glucan in the *Saccharomyces cerevisiae* cell wall, Journal of Cell Biology, vol. 128(3), pp. 333-340 (1995).
English language Abstract of JP 2000-102387.
Zaworski et al., *Antimicrob. Agents Chemother.* 34(4):660-662 (1990).
Ye et al., *Applied Microbiol. Biotechnol.* 54(1):90-96 (2000).
L. Popolo et al., "The Gas1 Glycoprotein, A Putative Wall Polymer Cross-linker", Biochimica et Biophysica Acta, vol. 1416, pp. 385-400 (1999).
S. Leidich et al., "Temperature-Sensitive Yeast GPI Anchoring Mutants GPI2 and GPI3 Are Defective in the Synthesis of N-Acetylglucosaminyl Phophatidylinositol" Journal of Biological Chemistry, vol. 270, No. 22, pp. 13029-13035 (1995).
K. Hamada et al., "Amino Acid Sequence Requirement for Efficient Incorporation of Glycosylphosphatidylinositol-associated Proteins into the Cell Wall of *Saccharomyces cerevisiae*", The Journal of Biological Chemistry, vol. 271, No. 41, pp. 26946-26953 (1998).
L. Heleen et al., "In Silico Identification of Glycosyl-phosphatidylinositol-anchored Plasma-membrane and Cell Wall Proteins of *Saccharomyces cerevisiae*", Yeast, vol. 13, pp. 1477-1489 (1997).

(Continued)

*Primary Examiner*—Ralph Gitomer
*Assistant Examiner*—Bin Shen
(74) *Attorney, Agent, or Firm*—Greenblum & Bernstein, P.L.C.

(57) ABSTRACT

A method for screening an agent acting on a cell wall, which comprises the following steps of: (1) culturing a microorganism having a reporter protein fixed on a cell wall as a GPI-anchored protein in the presence of a test agent acting on a cell wall; (2) analyzing a saccharide chain of a substance derived from the reporter protein released in a culture fluid of the microorganism; and (3) estimating a targeting site of the test agent on the cell wall on the basis of information of the saccharide chain of the substance derived from the reporter protein obtained in the step (2). An agent acting on a cell wall directed to a particular targeting site can be efficiently screened by conveniently and suitably determining a targeting site of an agent having an inhibitory action on a cell wall.

17 Claims, 10 Drawing Sheets

OTHER PUBLICATIONS

Vectors for *E. coli*, "General Purpose Cloning Vectors: I-A-iv-20", Elsevier Science Publishers BV (1985).

Vectors for *E. coli*, "General Purpose Cloning Vectors: VI-A-i-2", Elsevier Science Publishers BV (1985).

Vectors for *E. coli*, "General Purpose Cloning Vectors: VI-A-i-5", Elsevier Science Publishers BV (1985).

T. Hughes, "Yeast and Drug Discovery", Funct. Integr. Genomics, vol. 2, pp. 199-211 (2002).

J. Sturtevant, "Translation Elongation-3-like Factors: Are They Rational Antifungal Targets?", Expert Opin. Ther. Targets, vol. 6, No. 5, pp. 545-553 (2002).

A. Ram et al., "Green Fluorescent Protein-Cell Wall Fusion Proteins are Covalently Incorporated into the Cell Wall of *Saccharomyces cerevisiae*" *FEMS Microbiology Letters* 162:249-255 (1998).

Comack, B. "Green Fluorescent Protein as a Reporter of Transcription and Protein Localization in Fungi" *Current Opinion in Microbiology* 1:406-410 (1998).

A. Ornelas-Sores et al., Journal of Biological Chemistry, vol. 269, No. 44, pp. 27246-27250, Nov. 4, 1994.

M. Gentzsch et al., EMBO J., vol. 15, No. 21, pp. 5752-5759, 1996.

A. Hausler et al., Proc. Natl. Acad. Sci. USA, vol. 89, pp. 6846-6850, Aug. 1992.

N. Dean, Biochimica et Biophysica Acta, vol. 1426, pp. 309-322, 1999.

P. Mazur et al., Mol. Cell. Biol., vol. 15, No. 10, pp. 5671-5681, Oct. 1995.

T. Roemer et al., Mol. Cell. Biol., vol. 13, No. 7, pp. 4039-4048, Jul. 1993.

S. Leidich et al., J. Biol. Chem., vol. 269, No. 14, pp. 10193-10196, Apr. 8, 1994.

L. Popolo et al., J. Bacteriol., vol. 175, No. 7, pp. 1879-1885, Apr. 1993.

V. Cid et al., Microbiological Reviews, vol. 59, pp. 345-386, Sep. 1995.

K. Redding et al., J. Cell. Biol., vol. 113, No. 3, pp. 527-538, May 1991.

\* cited by examiner

Fig. 4

```
ACTAGTATGCTTTTGCAAGCTTTCCTTTTCCTTTTGGCTGGTTTTGCAGCCAAAATATCT
     M  L  L  Q  A  F  L  F  L  L  A  G  F  A  A  K  I  S
/
SpeI
```

```
        70        80        90       100       110       120
GCATCAAAGAGCTCGCATGCCTGCAGGTCGACTCTAGAGGATCCCCGGGTACCGGTAGAA
 A  S  K  S  S  H  A  C  R  S  T  L  E  D  P  R  V  P  V  E
            /
            SacI
```

```
       130       140       150       160       170       180
AAAATGAGTAAAGGAGAAGAACTTTTCACTGGAGTTGTCCCAATTCTTGTTGAATTAGAT
 K  M  S  K  G  E  E  L  F  T  G  V  V  P  I  L  V  E  L  D
```

```
       190       200       210       220       230       240
GGTGATGTTAATGGGCACAAATTTTCTGTCAGTGGAGAGGGTGAAGGTGATGCAACATAC
 G  D  V  N  G  H  K  F  S  V  S  G  E  G  E  G  D  A  T  Y
```

```
       250       260       270       280       290       300
GGAAAACTTACCCTTAAATTTATTTGCACTACTGGAAAACTACCTGTTCCATGGCCAACA
 G  K  L  T  L  K  F  I  C  T  T  G  K  L  P  V  P  W  P  T
```

```
       310       320       330       340       350       360
CTTGTCACTACGTTAACTTATGGTGTTCAATGCTTTTCCCGTTATCCGGATCATATGAAA
 L  V  T  T  L  T  Y  G  V  Q  C  F  S  R  Y  P  D  H  M  K
```

```
       370       380       390       400       410       420
CGGCATGACTTTTTCAAGAGTGCCATGCCCGAAGGTTATGTACAGGAACGCACTATATCT
 R  H  D  F  F  K  S  A  M  P  E  G  Y  V  Q  E  R  T  I  S
```

```
       430       440       450       460       470       480
TTCAAAGATGACGGGAACTACAAGACGCGTGCTGAAGTCAAGTTTGAAGGTGATACCCTT
 F  K  D  D  G  N  Y  K  T  R  A  E  V  K  F  E  G  D  T  L
```

```
       490       500       510       520       530       540
GTTAATCGTATCGAGTTAAAAGGTATTGATTTTAAAGAAGATGGAAACATTCTCGGACAC
 V  N  R  I  E  L  K  G  I  D  F  K  E  D  G  N  I  L  G  H
```

```
       550       560       570       580       590       600
AAACTCGAGTACAACTATAACTCACACAATGTATACATCACGGCAGACAAACAAAAGAAT
 K  L  E  Y  N  Y  N  S  H  N  V  Y  I  T  A  D  K  Q  K  N
```

Fig. 5

```
          610       620       630       640       650       660
GGAATCAAAGCTAACTTCAAAATTCGCCACAACATTGAAGATGGATCCGTTCAACTAGCA
 G  I  K  A  N  F  K  I  R  H  N  I  E  D  G  S  V  Q  L  A 670       680       690       700       710       720
GACCATTATCAACAAAATACTCCAATTGGCGATGGCCCTGTCCTTTTACCAGACAACCAT
 D  H  Y  Q  Q  N  T  P  I  G  D  G  P  V  L  L  P  D  N  H 730       740       750       760       770       780
TACCTGTCGACACAATCTGCCCTTTCGAAAGATCCCAACGAAAAGCGTGACCACATGGTC
 Y  L  S  T  Q  S  A  L  S  K  D  P  N  E  K  R  D  H  M  V 790       800       810       820       830       840
CTTCTTGAGTTTGTAACTGCTGCTGGGATTACACATGGCATGGATGAGATCTGTAGTGTT
 L  L  E  F  V  T  A  A  G  I  T  H  G  M  D  E  I  C  S  V
                                                  /
                                                Bgl II 850       860       870       880       890       900
GATTTGGGTTCCGGAACTGAATCCAGTACTGCCTCTTCTAACGCTTCGGGGTCTTCTTCC
 D  L  G  S  G  T  E  S  S  T  A  S  S  N  A  S  G  S  S  S 910       920       930       940       950       960
AAGTCTAACTCCGGCTCTTCTGGTTCTTCCAGTTCTTCTTCTTCTTCAGCTTCATCT
 K  S  N  S  G  S  S  G  S  S  S  S  S  S  S  A  S  S 970       980       990      1000      1010      1020
TCATCTTCTAGCAAGAAGAATGCTGCCACCAACGTTAAAGCTAACTTAGCACAAGTGGTC
 S  S  S  S  K  K  N  A  A  T  N  V  K  A  N  L  A  Q  V  V 1030      1040      1050      1060      1070      1080
TTTACCTCCATCATTTCCTTATCCATTGCCGCTGGTGTCGGTTTTGCTTTGGTTTAAAAA
 F  T  S  I  I  S  L  S  I  A  A  G  V  G  F  A  L  V  *

1090      1100      1110      1120
GCTTCGACACATACATAATAACTCGATAAGCCGCGG
                                   /
                                 SacII
```

Fig. 6

```
         10        20        30        40        50        60
ACTAGTATGCTTTTGCAAGCTTTCCTTTTCCTTTTGGCTGGTTTTGCAGCCAAAATATCT
      M  L  L  Q  A  F  L  F  L  L  A  G  F  A  A  K  I  S
/
SpeI 70        80        90       100       110       120
GCATCAAAGAGCTCGCATGCCTGCAGGTCGACTCTAGAGGATCCCCGGGTACCGGTAGAA
 A  S  K  S  S  H  A  C  R  S  T  L  E  D  P  R  V  P  V  E
              /
            SacI 130       140       150       160       170       180
AAAATGAGTAAAGGAGAAGAACTTTTCACTGGAGTTGTCCCAATTCTTGTTGAATTAGAT
  K  M  S  K  G  E  E  L  F  T  G  V  V  P  I  L  V  E  L  D 190       200       210       220       230       240
GGTGATGTTAATGGGCACAAATTTTCTGTCAGTGGAGAGGGTGAAGGTGATGCAACATAC
 G  D  V  N  G  H  K  F  S  V  S  G  E  G  E  G  D  A  T  Y 250       260       270       280       290       300
GGAAAACTTACCCTTAAATTTATTTGCACTACTGGAAAACTACCTGTTCCATGGCCAACA
 G  K  L  T  L  K  F  I  C  T  T  G  K  L  P  V  P  W  P  T 310       320       330       340       350       360
CTTGTCACTACGTTAACTTATGGTGTTCAATGCTTTTCCCGTTATCCGGATCATATGAAA
 L  V  T  T  L  T  Y  G  V  Q  C  F  S  R  Y  P  D  H  M  K 370       380       390       400       410       420
CGGCATGACTTTTTCAAGAGTGCCATGCCCGAAGGTTATGTACAGGAACGCACTATATCT
 R  H  D  F  F  K  S  A  M  P  E  G  Y  V  Q  E  R  T  I  S 430       440       450       460       470       480
TTCAAAGATGACGGGAACTACAAGACGCGTGCTGAAGTCAAGTTTGAAGGTGATACCCTT
 F  K  D  D  G  N  Y  K  T  R  A  E  V  K  F  E  G  D  T  L 490       500       510       520       530       540
GTTAATCGTATCGAGTTAAAAGGTATTGATTTTAAAGAAGATGGAAACATTCTCGGACAC
 V  N  R  I  E  L  K  G  I  D  F  K  E  D  G  N  I  L  G  H 550       560       570       580       590       600
AAACTCGAGTACAACTATAACTCACACAATGTATACATCACGGCAGACAAACAAAAGAAT
  K  L  E  Y  N  Y  N  S  H  N  V  Y  I  T  A  D  K  Q  K  N 610       620       630       640       650       660
GGAATCAAAGCTAACTTCAAAATTCGCCACAACATTGAAGATGGATCCGTTCAACTAGCA
 G  I  K  A  N  F  K  I  R  H  N  I  E  D  G  S  V  Q  L  A
```

Fig. 7

```
           670       680       690       700       710       720
GACCATTATCAACAAAATACTCCAATTGGCGATGGCCCTGTCCTTTTACCAGACAACCAT
 D  H  Y  Q  N  T  P  I  G  D  G  P  V  L  L  P  D  N  H 730       740       750       760       770       780
TACCTGTCGACACAATCTGCCCTTTCGAAAGATCCCAACGAAAAGCGTGACCACATGGTC
 Y  L  S  T  Q  S  A  L  S  K  D  P  N  E  K  R  D  H  M  V 790       800       810       820       830       840
CTTCTTGAGTTTGTAACTGCTGCTGGGATTACACATGGCATGGATGAGATCTCTGAATCC
 L  L  E  F  V  T  A  A  G  I  T  H  G  M  D  E  I  S  E  S
                                                  /
                                                Bgl II 850       860       870       880       890       900
GCTGCCGCCATTTCTCAAATCACTGACGGTCAAATCCAAGCTACTACCACTGCTACCACC
 A  A  A  I  S  Q  I  T  D  G  Q  I  Q  A  T  T  T  A  T  T 910       920       930       940       950       960
GAAGCTACCACCACTGCTGCCCCATCTTCCACCGTTGAAACTGTTTCTCCATCCAGCACC
 E  A  T  T  T  A  A  P  S  S  T  V  E  T  V  S  P  S  S  T 970       980       990      1000      1010      1020
GAAACTATCTCTCAACAAACTGAAAATGGTGCTGCTAAGGCCGCTGTCGGTATGGGTGCC
 E  T  I  S  Q  Q  T  E  N  G  A  A  K  A  A  V  G  M  G  A 1030      1040      1050      1060      1070      1080
GGTGCTCTAGCTGCTGCTGCTATGTTGTTATAAGAAATCTCTGATTTTTTATAATATCTA
 G  A  L  A  A  A  A  M  L  L  *

1090      1100      1110      1120      1130      1140
TATGGCTTTTTTCAAAATTTTCGGTTTTACTAGGTAAGTGTTTGATTCTTTTCTTTTCGT 1150      1160      1170      1180      1190      1200
TAATATATTTTTACACATAATTTTAAATAATTTTTGTTATTTTGAATAGGTAGATACCAT 1210      1220      1230      1240
AAAAATAAAACACTTTTTACTTTAACGAGTCCGCGG
                                    /
                                  SacII
```

Difference in fluorescence 1,8: AY-10u (Parent strain)
2: AY-10d (ΔBCK1)
3: AY-10h (ΔFKS1)
4: AY-10a (ΔGAS1)
5: AY-10l (ΔGPI1)
6: AY-10b (ΔKEX2)
7: AY-10i (ΔKRE2)
9: AY-10k (ΔKRE6)
10: AY-10j (ΔMNN9)
11: AY-10e (ΔPMT1)
12: AY-10f (ΔPMT2)
13: AY-10g (ΔPMT4)
14: AY-10c (ΔSKN1)

1: no drug
2: SP 10μg/ml
3: SP 5μg/ml
4: SP 2.5μg/ml
5: SP 1.25μg/ml
6: TM 80μg/ml
7: TM 40μg/ml
8: TM 20μg/ml
9: AC 0.313μg/ml
10: AC 0.156μg/ml
11: AC 0.078μg/ml

METHOD FOR SCREENING AGENT ACTING ON CELL WALL

TECHNICAL FIELD

The present invention relates to a method for screening an agent acting on a cell wall utilizing a microorganism having a reporter protein such as a fluorescent protein fixed on a cell wall as a GPI-anchored protein.

BACKGROUND ART

Increasing tendency of incidence of deep fungal infections has been seen as the number of compromised patients increases, and therefore, effective therapeutic agents have been desired. Currently, only five antifungal agents for deep fungal infections have been launched in the market in Japan. Among them, three agents are azole-type agents (miconazole, fluconazole and itraconazole). Fluconazole, a most typical agent, has only a fungistatic action. Moreover, with increase of amount of the agent used, appearance of resistant fungi is concerned. Amphotericin B, a polyene antibiotic having a potent fungicidal effect, is highly toxic, and the agent cannot be always used safely. From these reasons, antifungal treatment of patients with deep fungal infections often results in a poor satisfactory level, and thus demands for novel fungicidal and fungiselective agents are urgent.

A cell wall which characteristically exists in fungal cells is an attractive target from a viewpoint of selectivity. In yeast, for example, major saccharide polymers constituting the cell wall include $(1,3)$-$\beta$-glucan, $(1,6)$-$\beta$-glucan, chitin and mannan. Among synthetic pathways of these saccharide polymers, the synthetic pathway of mannan commonly exists in animal cells and fungal cells and each biosynthetic pathway has high commonness, and therefore, it is considered generally difficult, although not absolutely impossible, to find a target specific to fungi. In the synthetic pathways of $(1,3)$-$\beta$-glucan and that of chitin, existence of enzymes specific to fungi and essential for their growth, such as the FKS gene group and the CHS gene group, has been elucidated, and research and development of antifungal agents targeting the enzymes are being conducted. Thus, candin antifungal agents having a $(1,3)$-$\beta$-glucan inhibitory action have been practically developed. The $(1,6)$-$\beta$-glucan synthetic pathway is also considered as specific to fungi, and existence of enzymes believed to be essential for growth of fungi has been elucidated based on results of genetic analyses. However, no assay system at an enzyme level has been established, and accordingly, no inhibitor against these enzymes has been reported. For this reason, no antifungal agent inhibiting this synthetic pathway has been known to date.

In general, proteins collectively called as GPI-anchored proteins extensively exist in eukaryotic cells. These are fixed on cell membranes via GPI anchors (Ferguson, M. A., et al., Ann. Rev. Biochem., 57, pp.285-320, 1988). Each GPI-anchored protein has relatively hydrophobic signal peptide regions at both ends of the N- and C-terminals. These signals are cleaved by post-translational modification, and with addition of a GPI anchor to the C-terminus, the protein is fixed on the ER (rough endoplasmic reticulum) membrane. Then, the GPI-anchored protein fixed on the ER membrane is transported on the membrane, and then further fixed on the cell membrane (Ferguson, M. A., et al., Ann. Rev. Biochem., 57, pp.285-320, 1988; Lu, C. F., et al., Mol. Cell Biol., 14, pp.4825-4833, 1994).

In Saccharomyces cerevisiae, a part of the GPI anchor is further cleaved from some of the GPI-anchored proteins fixed on the cell membrane, and then the protein is further fixed on the cell wall via $(1,6)$-$\beta$-glucan as an anchor (Lu, C. F., et al., Mol. Cell Biol., 14, pp.4825-4833, 1994; Kollar, R., et al., J. Biol. Chem., 272, pp.17762-17775, 1997).

This means that, in Saccharomyces cerevisiae, two kinds of GPI-anchored proteins exist; one is fixed on the cell membrane and the other in the cell wall. This difference in localization is expected to be regulated by the difference in the signal peptide at the C-terminus (Hamada, K., et al., Mol. Gen. Genet., 258, pp.53-59, 1998; Caro, L., Yeast, 13, pp.1477-1489, 1997). Recently, creation of an yeast having an arbitrary exogenous protein fixed on the cell wall (arming yeast) was reported by utilizing the localization mechanism of proteins on cell walls (Varrt, J. M. V. D., et al., Appl. Environ. Microbiol., 63, pp.615-620, 1997; Murai, T., et al., Appl. Environ. Microbiol., 63, pp.1362-1366, 1997).

As described above, $(1,6)$-$\beta$-glucan has a function as an anchor for fixing the GPI-anchored proteins on the cell walls, and analytical results so far obtained reveal that, when biosynthesis of $(1,6)$-$\beta$-glucan is inhibited by gene disruption, these proteins are extracellularly released (Lu, C. F., et al., Mol. Cell Biol., 14, pp.4825-4833, 1994; Lu, C. F., et al., J. Cell. Biol., 128, pp.333-340, 1995).

Recently, Tsuchiya et al. reported construction of an expression system of a reporter protein bound with staphylococcus cell wall peptide glycan (The Pharmaceutical Society of Japan, The 120th Annual Meeting, Abstracts 2, p.153, Lecture No. 30 [PB] 15-71). This system comprises cephalosporinase as a reporter protein anchored on a cell wall of gram-positive bacterium. However, application of this system has not been clarified, and the publication neither suggests nor teaches that the system can be used for screening of an agent acting on a cell wall.

Further, no method has been known so far as a method for conveniently and accurately estimating targeting sites of cell wall-acting agents, except a method for screening agents relating to cell walls such as $(1,3)$-$\beta$-glucan and chitin. A method for screening an agent acting on a particular targeting site cannot be applied for screening of agents acting on the other targeting site.

DISCLOSURE OF THE INVENTION

An object of the present invention is to provide a method for screening an agent acting on a cell wall. More specifically, the object of the present invention is to provide a method for screening an agent acting on a cell wall, wherein each targeting site of agents having an inhibitory action on a cell wall is conveniently and suitably determined, thereby agents acting on a particular targeting site are efficiently screened.

The inventors of the present invention previously found that an agent having a selective inhibitory action on a cell wall, for example, an agent having a selective inhibitory action on an enzyme for biosynthesis of $(1,6)$-$\beta$-glucan that constitutes the cell wall, should be successfully screened by preparing two kinds of yeasts each having an easily detectable protein (reporter protein) fixed on the cell membrane or cell wall (referred to as "membrane-type arming yeast" and "wall-type arming yeast", respectively), and using a criterion that a release of the reporter protein is occurred substantially only from the wall-type arming yeast (PCT/JP01/3630).

The inventors of the present invention further conducted various researches to achieve the foregoing object. As a result, they found that a molecular weight of each saccharide chain constituting a cell wall, that attached to a released reporter protein, is different to each other depending on a targeting site of an agent having a selective inhibitory action on a cell wall, and thus the targeting site of the agent can be estimated by measuring the molecular weight of a released reporter protein. That is, they found a phenomenon that each saccharide chain of a released reporter protein is different from each other depending on a targeting site of an agent having a selective inhibitory action on a cell wall. The present invention was achieved on the basis of these findings.

The present invention thus provides a method for screening an agent acting on a cell wall, which comprises the steps of:
(1) culturing a microorganism in the presence of a test agent acting on a cell wall, wherein said microorganism has a reporter protein fixed on a cell wall as a GPI-anchored protein;
(2) analyzing a saccharide chain of a substance derived from the reporter protein released in a culture fluid of the microorganism; and
(3) estimating a targeting site of the test agent on the cell wall on the basis of information of the saccharide chain of the substance derived from the reporter protein obtained in the step (2). This method is preferably used for screening of agents directed to a desired targeting site among from agents acting on a cell wall.

As preferred embodiments of the aforementioned invention, provided are the aforementioned method, wherein the analysis of the saccharide chain of the substance derived from the reporter protein is performed by measuring molecular weight of the substance derived from the reporter protein; the aforementioned method, which uses a microorganism having a reporter protein fixed to (1,6)-β-glucan of the cell wall; the aforementioned method, wherein the microorganism is yeast; the aforementioned method, wherein the reporter protein is a fluorescent protein; the aforementioned method, wherein the fluorescent protein is a green fluorescent protein; and the aforementioned method, wherein the inhibitory action on the cell wall is an inhibitory action against a biosynthetic process of the cell wall and/or a biosynthetic enzyme of the saccharide chain (enzyme involved in extension of the saccharide chain). The agent acting on a cell wall is preferably an antifungal agent.

In a further preferred embodiment of the present invention, the method further comprises a step of screening an agent acting on a cell wall before the aforementioned steps. In this embodiment, agents acting on a cell wall are first screened by the following steps of:
(A1) culturing each of a microorganism having a reporter protein fixed on a cell wall as a GPI-anchored protein and a microorganism having a reporter protein fixed on a cell membrane as a GPI-anchored protein in the presence of a test agent;
(A2) determining a substance derived from the reporter protein released into each culture fluid of the microorganism cultured; and
(A3) judging that the test agent is an agent having a selective inhibitory action on a cell wall when the substance derived from the reporter protein is released from the microorganism having the reporter protein fixed on the cell wall into the culture fluid and the substance derived from the reporter protein is not substantially released from the microorganism having the reporter protein fixed on the cell membrane into the culture fluid;
and then the aforementioned steps (1) to (3) can be performed for agents determined to be agents having a selective inhibitory action on a cell wall in the step (A3) to screen an agent directed to a desired targeting site from the above agents.

From another aspect, the present invention provides a method for estimating a targeting site of an agent acting on a cell wall, which comprises the steps of:
(1) culturing a microorganism having a reporter protein fixed on a cell wall as a GPI-anchored protein in the presence of a test agent acting on a cell wall;
(2) analyzing a saccharide chain of a substance derived from the reporter protein released in a culture fluid of the microorganism; and
(3) estimating a targeting site of the test agent on the cell wall on the basis of information of the saccharide chain of the substance derived from the reporter protein obtained in the step (2) (in particular, molecular weight, molecular weight pattern or the like).

BRIEF DESCRIPTION OF THE DRAWINGS

FIG. 4 shows the nucleotide sequence (SEQ ID NO: 1) (number of nucleotides: 1116) of the gene introduced into the AY-15 strain, recognition sites of the restriction enzymes and amino acid sequence (SEQ ID NO: 3) (one letter code) encoded by the gene. The figure shows the nucleotides up to the nucleic acid number 600 of SEQ ID NO: 1.

FIG. 5 shows the nucleotide sequence (SEQ ID NO: 1) (number of nucleotides: 1116) of the gene introduced into the AY-15 strain, recognition sites of the restriction enzymes and amino acid sequence (SEQ ID NO: 3) (one letter code) encoded by the gene. The figure shows the nucleotides of the nucleic acid numbers from 601 to 1116 of SEQ ID NO: 1.

FIG. 6 shows the nucleotide sequence (SEQ ID NO: 2) (number of nucleotides: 1236) of the gene introduced into the AY-14 strain, recognition sites of the restriction enzymes and amino acid sequence (SEQ ID NO: 4) (one letter code) encoded by the gene. The figure shows the nucleotides up to the nucleic acid number 660 of SEQ ID NO: 2.

FIG. 7 shows the nucleotide sequence (SEQ ID NO: 2) (number of nucleotides: 1236) of the gene introduced into the AY-14 strain, recognition sites of the restriction enzymes and amino acid sequence (SEQ ID NO: 4) (one letter code) encoded by the gene. The figure shows nucleotides of the nucleic acid numbers from 661 to 1236 of SEQ ID NO: 2.

BEST MODE FOR CARRYING OUT THE INVENTION

Figure 1:
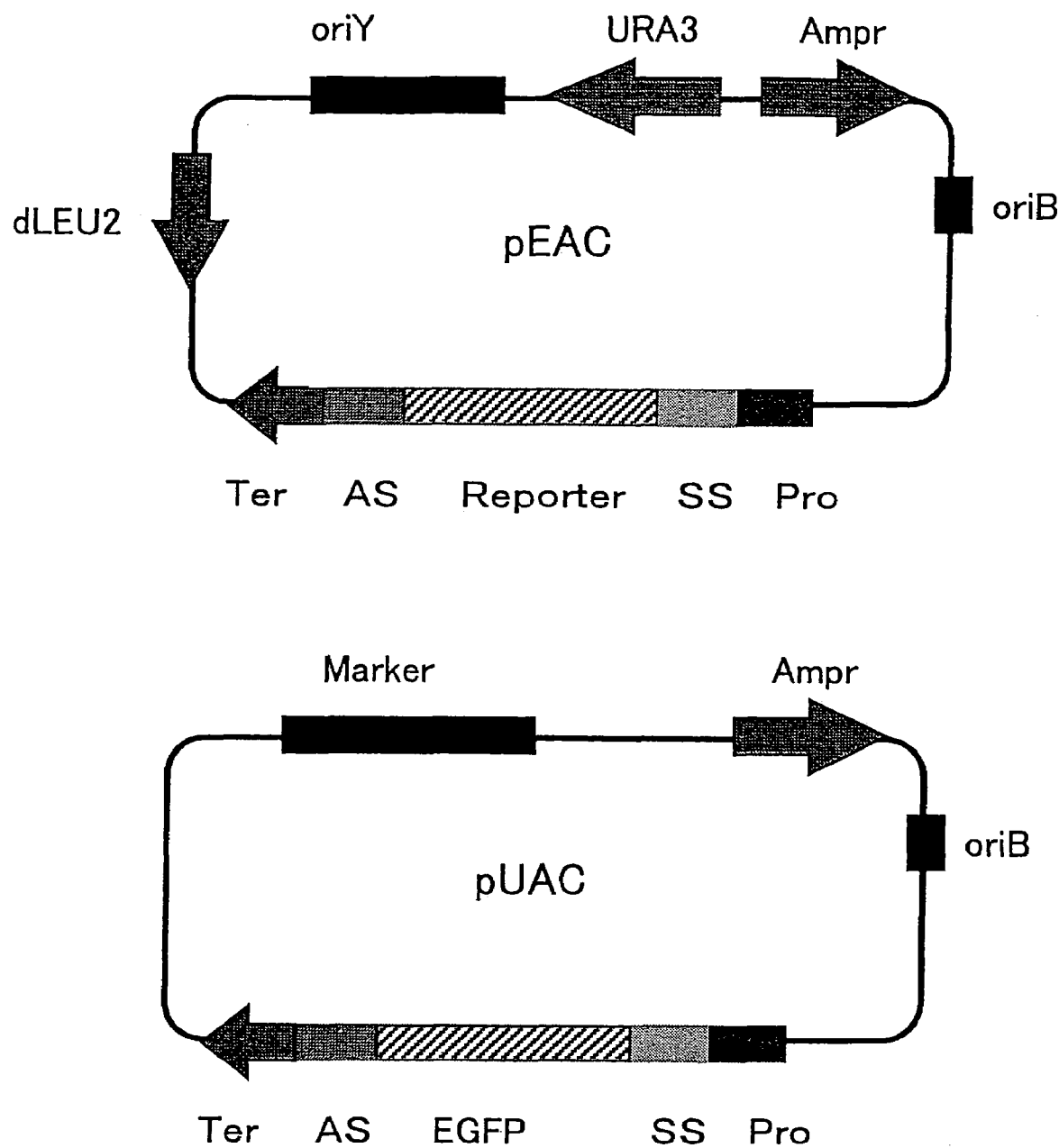
FIG. 1 shows the structures of major plasmids (pEAC and pUAC) used in the example.

The screening method of the present invention can be preferably used for screening of an agent directed to a particular targeting site among from agents acting on a cell wall. In general, agents acting on a cell wall, preferably agents having a selective inhibitory action on a cell wall, are selected from a library including numerous compounds or the like as a primary screening, and then the method can be used for purposes such as for identification of each target site of the agents or a further screening of an agent directed to a particular targeting site therefrom. However, uses of the method of the present invention are not limited to those mentioned above, and the method of the present invention may be directly applied to a test agent for the purpose of confirming the targeting site of the agent without performing the aforementioned primary screening. It should be understood that such embodiment also falls within the scope of the present invention.

In the present specification, the wording "acting on a cell wall" means, for example, to act on one or more of the following enzymes and interfere with actions or functions of the enzymes.

(a) enzymes for synthesis of components constituting cell wall (saccharide polymers) of microorganisms;

(b) enzymes assisting actions of enzymes for synthesis of components constituting cell walls (saccharide polymers) of microorganisms;

(c) enzymes inhibiting the functions of enzymes for synthesis of components constituting cell walls (saccharide polymers) of microorganisms;

(d) processes required for the enzymes belonging to the class of the aforementioned (b) and (c) to assist or inhibit the actions of the enzyme for synthesis of the aforementioned (a), and enzymes involved in the processes;

(e) processes acting in crosslinking between different saccharide polymers and enzymes involved in the processes;

(f) processes for anchoring components constituting cell walls on the cell walls (e.g., GPI proteins present in cell walls) besides the saccharide polymers, and enzymes involved in the processes;

(g) processes of normal construction of saccharide polymers in cell walls and enzymes involved in the processes;

(h) processes and pathways for regulating synthesis of cell walls and enzymes involved in the processes;

(i) processes acting in cell division of microbial cells and enzymes involved in the processes;

(j) processes of changing the shapes of microbial cells and enzymes involved in the processes;

(k) processes of digesting constructed cell walls of microbial cells and enzymes involved in the processes;

(l) processes in which microorganisms significantly change cell wall compositions in response to changes in the external environment and enzymes involved in the processes; and (m) other processes of construction and synthesis of microbial cell walls and change of cell wall structures, besides the aforementioned examples, and enzymes involved in the processes.

Further, in the specification, the wording "having a selective inhibitory action on a cell wall" means to have a specific inhibitory action on the events described in the aforementioned (a) to (m) including synthesis, decomposition and the like of cell walls. In the specification, the term "agent" is used so as to encompass any substances having a biological action including low molecular compounds to macromolecular compounds as well as natural substances, proteins or a part thereof, polypeptides, nucleic acids such as oligonucleotides and the like. The term "agent" should not be construed in any limitative sense, and the term should be construed in its broadest sense.

Prior to performing the method of the present invention, agents acting on a cell wall are preferably screened from a compound library (in the specification, screening performed for the aforementioned purpose is also referred to as the "primary screening). This screening can be usually performed according to the method described in PCT/JP01/3630. More specifically, agents acting on a cell wall can be selected by a screening method comprising the following steps of:

(A1) culturing each of a microorganism having a reporter protein fixed on a cell wall as a GPI-anchored protein and a microorganism having a reporter protein fixed on a cell membrane as a GPI-anchored protein in the presence of a test agent;

(A2) determining a substance derived from the reporter protein released into each culture fluid of the microorganism cultured; and (A3) judging that the test agent is an agent having a selective inhibitory action on a cell wall when the substance derived from the reporter protein is released from the microorganism having the reporter protein fixed on the cell wall into the culture fluid and the substance derived from the reporter protein is not substantially released from the microorganism having the reporter protein fixed on the cell membrane into the culture fluid.

In the aforementioned primary screening, a microorganism having a reporter protein fixed on a cell wall as a GPI-anchored protein and a microorganism having a reporter protein fixed on a cell membrane as a GPI-anchored protein are each cultured in the presence of a test agent, and then the substances derived from the reporter proteins released into the culture fluid are determined. The conditions including type of the medium, a temperature, a cultivation period of time and the like can be appropriately chosen depending on the types of the microorganisms used. A specific culture method wherein an yeast is used as the microorganism is specifically described in PCT/JP01/3630. The term "GPI-anchored protein" used in the specification does not mean any particular protein, and it should not be construed in any limitative way.

The reporter proteins are not particularly limited so long as their properties are already elucidated, and their types are not particularly limited so long as they are proteins that can be detected by ordinary means, for example, spectroscopic means such as fluorometry, high performance liquid chromatography, mass spectrometry or biochemical means such as enzymatic reactions. For example, a fluorescent protein and the like can be preferably used. For example, a green fluorescent protein (GFP) or a mutant thereof (EGFP: Dormack, B. P., et al., Gene, 173, pp.33-38, etc.) is preferably used. In the specification, the term "green fluorescent protein" is used so as to encompass GFP and mutants thereof. The types of the microorganisms are not particularly limited so long as they are eukaryotic cell microorganisms having a GPI-anchored protein. For example, yeasts such as S. cerevisiae are preferably used.

In yeast, it is known that a part of some of GPI-anchored proteins fixed on cell membrane are further fixed on the cell wall via (1,6)-β-glucan as an anchor (Lu, C. F., et al., Mol. Cell Biol., 14, pp.4825-4833, 1994; Kollar, R., et al., J. Biol. Chem., 272, pp.17762-17775, 1997). In addition, a method is known for fixing an enzyme on a cell wall of microorganism by producing a fusion protein (Chris et. al, International Patent Unexamined Publication in Japanese (KOHYO) No. 7-508652). On the basis of these findings, methods for fixing an exogenous protein on a cell wall of an yeast have been developed (Varrt, J. M. V. D., et al., Appl. Environ. Microbiol., 63, pp.615-620, 1997; Murai, T., et al., Appl. Environ. Microbiol., 63, pp.1362-1366, 1997). The GPI-anchored protein is also referred to as GPI anchor-type protein, and may also sometimes be referred to as glycosylphosphatidylinositol anchor type protein, phosphatidylinositol anchor type protein, PI anchor type protein or the like.

Therefore, yeasts are preferably used as the microorganism. When yeasts are used, a yeast in which a reporter protein is fixed on a cell wall or cell membrane as the GPI-anchored protein can be prepared according to the methods described in the aforementioned publications. Specific procedures thereof are described in the example of PCT/JP01/3630, and those skilled in the art can produce desired microorganisms according to the methods described in the aforementioned publication.

In the screening method described in the specification, a substance derived from a reporter protein is an aggregate of a single protein or two or more kinds of proteins which is released from cell walls by an action of an agent and contains the whole reporter protein or a major part thereof (in the specification, the term "substance derived from a reporter protein" means either a single kind of substance or a mixture of multiple kinds of substances, unless otherwise specifically indicated). As will be described later, when the reporter protein is fixed on a cell wall, a substance derived from a reporter protein is produced each having a characteristic saccharide chain depending on a targeting site of an agent acting on a cell wall.

In the culture step of the aforementioned primary screening (in the primary screening, the substance derived from a reporter protein includes a substance released from a cell wall, as well as a protein(s) released from a cell membrane corresponding to the substance derived from the reporter protein released from a cell wall), when release of the substance derived from a reporter protein into the culture fluid is observed, it can be interpreted that the cell wall or cell membrane of the microorganism was damaged by an action of the test agent, which results in the release of the substance derived from a reporter protein (Lu, C. F., et al., Mol. Cell Biol., 14, pp.4825-4833, 1994; Lu, C. F., et al., J. Cell. Biol., 128, pp.333-340, 1995). For example, when an agent that selectively damages a cell wall is screened as an agent having selective toxicity for fungi, a criterion that the substance derived from a reporter protein is released from the microorganism having the reporter protein fixed on the cell wall into the culture fluid, whilst the substance derived from a reporter protein is not substantially released from the microorganism having the reporter protein fixed on the cell membrane into the culture fluid, and an agent that satisfies the criterion can be chosen. An agent determined as positive for the criterion can be estimated as an agent having a selective inhibitory action on the biosynthesis of the cell wall.

In the primary screening, for the measurement of the substance derived from a reporter protein, an appropriate method can be chosen depending on the type and properties of the reporter protein. For example, when a green fluorescent protein is used as the reporter protein, release of the substance derived from a reporter protein can be determined by measuring the fluorescent spectrum in the culture fluid.

The method of the present invention is preferably used for screening of an agent directed to a particular targeting site among from agents acting on a cell wall chosen by the aforementioned primary screening, and characterized by comprising the following steps of:
(1) culturing a microorganism having a reporter protein fixed on a cell wall as a GPI-anchored protein in the presence of a test agent acting on a cell wall;
(2) analyzing a saccharide chain of a substance derived from the reporter protein released into a culture fluid of the microorganism; and
(3) estimating a targeting site of the test agent on the cell wall on the basis of information of the saccharide chain of the substance derived from the reporter protein obtained in the step (2).

The microorganism used in the method of the present invention is, among those referred to in the aforementioned explanation about the primary screening, a microorganism wherein a reporter protein is fixed on a cell wall as a GPI-anchored protein. According to a preferred embodiment, a microorganism wherein a reporter protein is fixed to (1,6)-β-glucan of cell walls or the like can be used. As referred to in the explanation about the primary screening, yeasts are preferably used as the microorganism. In the microorganism used in the method of the present invention, a fluorescent protein is preferably used as the reporter protein, and a green fluorescent protein is most preferably used.

The method of the present invention utilizes the fact that the saccharide chain that binds to a substance derived from a reporter protein changes depending on a difference of a targeting site of an agent acting on a cell wall, and the method is characterized in estimating a targeting site of a test agent by analyzing the saccharide chain, preferably, determining the molecular weight of the substance derived from the reporter protein (in particular, the molecular weight or molecular weight pattern).

In general, multiple kinds of saccharide chains such as N-glycosyl chain and O-glycosyl chain, as well as (1,6)-β-glucan and/or (1,3)-β-glucan involved in the anchoring, bind to the reporter protein fixed to a cell wall as a GPI-anchored protein. Agents acting on a cell wall such as (1,6)-β-glucan synthesis inhibitor, (1,3)-β-glucan synthesis inhibitor, mannan synthesis inhibitor (N-type saccharide chain or O-type saccharide chain), hetero saccharide chain crosslinking inhibitor, inhibitor for regulation of saccharide chain synthesis and GPI anchor synthesis inhibitor each have an ability to act on the aforementioned microorganism to allow release of a substance derived from a reporter protein. Since these agents act on the saccharide chains at different targeting sites, the saccharide chains that bind to the aforementioned substance derived from a reporter protein characteristically change depending on the difference of the targeting sites of the agents. As a result, the aforementioned substances derived from a reporter protein will have a characteristic saccharide chain fragment (or include deletion of a particular saccharide chain) depending on the targeting sites of the agents.

In the method of the present invention, the method for analyzing the saccharide chain of a substance derived from a reporter protein is not particularly limited. The term "analysis of saccharide chain" used in the specification should be construed in its broadest sense including determination of the molecular weight of the whole substance derived from the reporter protein, as well as determination of molecular weight or structure of the saccharide chain portion. Any method enabling verification of difference in the saccharide chain may be used. Most conveniently, the saccharide can be analyzed by determining the molecular weight of the whole substance derived from a reporter protein by electrophoresis using polyacrylamide gel or the like. Molecular weight distribution of the substance derived from the reporter protein reflecting the difference in the saccharide chain can be visually examined by using a technique well known and commonly used by those skilled in the art such as Western blotting. The term "determination of molecular weight" used in the specification may be construed to cover any means providing information sufficient for comparison of molecular weights, and the term should not be construed in any limitative way.

The method of the present invention can be most preferably used for a screening of, for example, an agent having an inhibitory action on the biosynthesis of (1,6)-β-glucan, or an agent having an inhibitory action on one or more enzymes involved in the biosynthesis of (1,6)-β-glucan, among from agents acting on a cell wall. Further, the method of the present invention also enables screening of a (1,3)-β-glucan biosynthesis inhibitor or an agent inhibiting synthesis or construction of cell walls by another action (of which targeting site may be unknown). Specific examples of the agent acting on a cell wall include antifungal agents and the like. However, agents that can be screened by the method of the present invention are not limited to antifungal agents.

EXAMPLES

The present invention will be explained more specifically with reference to the following examples. However, the scope of the present invention is not limited to this example.

Example 1 (Reference Example)

(1) Materials and Methods (A) Strains Used and Transformation

*Escherichia coli* strains JM109, TOP10F' and DH5 α, and *S. cerevisiae* strains YPH500 (MAT α ade2, his3, leu2, lys2, trp1, ura3), IFO 0565, IFO 1226 and KRE6-disrupted strain were used. Transformation was performed according to a known method or by using a yeast transformation kit (Invitrogen, Carlsbad, Calif., USA) according to the packaged manual.

(B) Agents Used

The agents shown below were used.

TABLE 1

| Agent | Acronym | Action |
|---|---|---|
| Aculeacin A | AC | Inhibition of cell wall ((1,3)- β-glucan) synthesis |
| Tunicamycin | TM | Inhibition of cell wall (N-type saccharide chain) synthesis |
| Nikkomycin Z | NM | Inhibition of cell wall (chitin) synthesis |
| Calcofluor white | CW | Physical adsorption to cell wall |
| Congo red | CR | Physical adsorption to cell wall |
| Amphotericin B | AMPH | Damage of cell membrane (binding to ergosterol) |
| Fluconazole | FCZ | Inhibition of cell membrane (ergosterol) synthesis |

TABLE 1-continued

| Agent | Acronym | Action |
|---|---|---|
| Aureobasidin | AB | Inhibition of cell membrane (sphingolipid) synthesis |
| Cerulenin | CE | Inhibition of cell membrane (fatty acid) synthesis |
| Salinomycin | SM | Damage of cell membrane (ionophore) |
| Flucytosine | 5-FC | Inhibition of nucleic acid synthesis |
| Zeocin | ZE | Binding to nucleic acid |
| Netropsin | NE | Inhibition of nucleic acid synthesis |
| Cycloheximide | CH | Inhibition of protein synthesis |
| Azaserine | AS | Inhibition of protein synthesis |
| Bromoconduritol | BC | Inhibition of mannosidase |
| Caffeine | CA | Intracellular information transmission (c-AMP) inhibition |

(C) Oligonucleotides

The following oligonucleotides were used in the experiment. M13 universal primer and M13 reverse primer were purchased from Pharmacia, and the other oligonucleotides were synthesized for use. These oligonucleotides can be utilized as genes used to fix a reporter protein on a cell wall or cell membrane of microorganism as a GPI-anchored protein.

(SEQ ID NO: 5)
GFP-SM2
(5'-GGCATGGATGAGATCTACAAATAATG-3')

(SEQ ID NO: 6)
GFP-SM3
(5'-CATGATTACGCCGAGCTCGCATGCCTG-3')

(SEQ ID NO: 7)
GFP-SM4
(5'-CAACACTTGTCACTACGTTAACTTATGGTGTTCAATG-3')

(SEQ ID NO: 8)
YEX-SM2
(5'-CCTGTGATTTCTCCAGCTCGAATTC-3')

(SEQ ID NO: 9)
YEX-SM3
(5'-GATTCATTAATGCATGCTGGCACGACAGG-3')

(SEQ ID NO: 10)
YEX-SM4
(5'-GATTCATTAATGCAGCTGGCACGAC-3')

(SEQ ID NO: 11)
YEX-SM5
(5'-CTCACGGTATCGCCCTCGAGATCTCTGAATCC-3')

(SEQ ID NO: 12)
YEX-SM6
(5'-GAGACCCTCTTCTGAGCTCTCTGAATCC-3')

(SEQ ID NO: 13)
YEX-SM7
(5'-AAACCAAAAGATCGACTAGTATAAAATGAATATA-3')

(SEQ ID NO: 14)
YEX-SM8
(5'-CATTAATGCATGCTGGCACGAC-3')

(SEQ ID NO: 15)
YEX-SM9
(5'-CTTTAACGAGTCCGCGGATTTCTCCAGCTCG-3')

(SEQ ID NO: 16)
SUC2-sen1
(5'-GCACTAGTATGCTTTTGCAAGCTTTCCTTTTC-3')

(SEQ ID NO: 17)
SUC2-anti2

-continued (5'-GCGAGCTCTTTGATGCAGATATTTTGGCTGCAA-3')

(SEQ ID NO: 18)
GAS1-sen1
(5'-GCAGATCTGTAGTGTTGATTTGGGTTCCGG-3')

(SEQ ID NO: 19)
GAS1-anti3
(5'-GCCCGCGGCTTATCGAGTTATTATGTATGTGTCGAAGC-3')

(SEQ ID NO: 20)
CWP2-sen1
(5'-GCAGATCTACTTTGTTGCCGCTGAATCCG-3')

(SEQ ID NO: 21)
CWP2-anti1
(5'-GCGAATTCGAGAAATCACAGGACTCGTTAAAG-3')

(SEQ ID NO: 22)
MEL1-sen1
(5'-GCGAATTCGAGAGCAACGGTAATAAAAGCAACGACG-3')

(SEQ ID NO: 23)
MEL1-sen3
(5'-CGGAGCTCGGTGTCTCCGAGTTACAATGGC-3')

(SEQ ID NO: 24)
MEL1-anti1
(5'-GCAGATCTAGAAGGCGATACCGTGAGCTGGAAC-3')

(SEQ ID NO: 25)
MEL1-anti2
(5'-CGGAGCTCCATCAATACTTCTCGCCCTGCT-3')

(SEQ ID NO: 26)
MEL1-anti3
(5'-GCAGATCTAAGAAGAGGGTCTCAACCTATAGAAG-3')

M13 universal primer and M13 reverse primer (D) Plasmids

By using pUC19, YEp13, YEp24 (for these, see Pouwels, P. H. et al., Cloning vectors, Elsevier Science Publishers B. V., 1985), pYPR2831 (Horiuchi, H. et al., Agric. Biol. Chem., 54, 1771-1779, 1990), pGFPuv (Clontech, Palo Alto, Calif., USA) and pYEX-S1 (Amrad, Victoria, Australia), the following plasmids were prepared and used. These plasmids include recombinant vectors containing the genes used to fix a reporter protein on a cell wall or cell membrane of microorganism as a GPI-anchored protein. pGEM-T Vector System (Promega, Madison, Wis., USA) was used for subcloning of PCR products, and Transformer Site-Directed Mutagenesis Kit (Clontech) was used for introduction of mutations. Recovery of DNA fragments from agarose, dephosphrylation, blunt-ending, ligation and digestion with restriction enzymes were performed according to conventional methods. The structures of major plasmids are shown in FIG. 1. In the figure, oriB represents the replication origin of Escherichia coli, oriY represents the replication origin of baker's yeast, Ampr represents ampicillin resistance gene, dLEU2 represents a partially deficient marker of LEU2, Pro represents a phosphoglycerate kinase promoter, SS represents a secretory signal, and Ter represents a phosphoglycerate kinase terminator.

pUXS1: A fragment obtained by digesting YEp24 with HindIII was inserted into the HindIII site of pUC19.

pUXS2: A fragment obtained by digesting YEp13 with XhoI and SalI was inserted into the SalI site of pUC19.

pUAC1: A part of CWP2 (Varrt, J. M. et al., J. Bacteriol., 177, 3104-3110, 1995) was amplified by PCR (template: YPH500 strain chromosomal DNA, primers: CWP2-sen1 and CWP2-anti1) and subcloned into PGEM-T.

pUAC1a: pUAC1 was digested with EcoRI and PstI and then self-ligated.

pUAC3: A part of MELL (Liljestrom, P. L., Nucl. Acids Res., 13, pp.7257-7268, 1985) was amplified by PCR (template: IFO 0565 strain chromosomal DNA, primers: MEL1-sen1 and MEL1-anti1) and subcloned into pGEM-T.

pUAC5a: A fragment obtained by digesting pUAC3 with ScaI and BglII was inserted into the ScaI and BglII sites of pUAC1a.

pUAC8: A part of MELL was amplified by PCR (template: IFO 1226 strain chromosomal DNA, primers: MEL1-sen3 and MEL1-anti1) and subcloned into pGEM-T.

pUAC12: A part of SUC2 (Taussig, R. et al., Nucl. Acids Res., 11, pp.1943-1954, 1983) was amplified by PCR (template: YHP500 strain chromosomal DNA, primers: SUC2-sen1 and SUC2-anti2) and subcloned into pGEM-T.

pUAC13: A part of MEL1 was amplified by PCR (template: IFO 0565 strain chromosomal DNA, primers: MEL1-sen3 and MEL1-anti3) and subcloned into pGEM-T.

pUAC14: A mutation was introduced into pGFPuv (primers: GFP-SM2 and GFP-SM3).

pUAC15: pEAC8a was digested with StuI and self-ligated.

pUAC15a: A mutation was introduced into pUAC15 (primers: YEX-SM4 and YEX-SM7).

pUAC16: A fragment obtained by digesting pUAC12 with NaeI and SpeI was inserted between the SpeI and StuI sites of pUAC15a.

pUAC19: A fragment obtained by digesting pUXS1 with EcoRV and PvuII was inserted into the EcoRV site of pEAC12.

pUAC19a: A mutation was introduced into pUAC19 (primers: GFP-SM4, YEX-SM8 and YEX-SM9).

pUAC20: A fragment obtained by digesting pUXS2 with EcoRV and PvuII was inserted into the EcoRV site of pEAC12.

pUAC20a: A mutation was introduced into pUAC20 (primers: GFP-SM4, YEX-SM8 and YEX-SM9).

pUAC21: A fragment obtained by digesting pYPR2831 with PstI was blunt-ended and inserted into the EcoRV site of pEAC12.

pUAC21a: A fragment obtained by digesting pUAC19a with SacI and BglII was inserted between the SacI and BglII sites of pUAC21.

pUAC28: A part of GAS1 (Vai, M., et al., J. Biol. Chem., 266, 12242-12248, 1990) was amplified by PCR (template: YPH500 strain chromosomal DNA, primers: GAS1-sen1 and GAS1-anti3) and subcloned into pGEM-T.

pUAC29b: A fragment obtained by digesting pUAC28 with BglII and SacII was inserted between the BglII and SacI sites of pUAC20a.

pUAC30b: A fragment obtained by digesting pUAC29b with BglII and BamHI was inserted into the BglII site of pUAC19a.

pUAC31b: A fragment obtained by digesting pUAC29b with BglII and BamHI was inserted into the BglII site of pUAC21a.

pEAC3: A fragment obtained by digesting pUAC5a with EcoRI and SalI was inserted between the EcoRI and SalI sites of pYPR2831.

pEAC6: A part of pEAC3 was amplified by PCR (template: pEAC3, primers: MEL1-sen3 and MEL1-anti2) and subcloned into pGEM-T, and a fragment obtained by digesting the obtained plasmid with SacI was inserted into the SacI site of pYEX-S1.

pEAC6a: A mutation was introduced into pEAC6 (primers: YEX-SM2 and YEX-SM3).

pEAC7: A fragment obtained by digesting pUAC8 with SacI and BglII was inserted between the SacI and BglII sites of pEAC6a.

pEAC7a: A mutation was introduced into pEAC7 (primers: YEX-SM4 and YEX-SM5).

pEAC8: A fragment obtained by digesting pUAC13 with SacI and BglII was inserted between the SacI and BglII sites of pEAC6a.

linearizing a plasmid obtained by inserting the expression cassette into a YIp type vector (pUAC19a, pUAC20a or pUAC21a) and then introducing into chromosomal DNA of each strain (AY-2, AY-5, AY-16, AY-14 or AY-17 strain). Membrane-type arming yeast (AY-12 or AY-15 strain) was prepared by replacing the GPI anchoring signal with any of those derived from GAS1 (pUAC29b, pUAC30b or pUAC31b). The prepared strains are shown in Table 2.

TABLE 2

| Yeast strain | Genotype | Phenotype | Gene manipulation |
|---|---|---|---|
| YPH500 (parent strain) | MATα ade2, his3, leu2, lys2, trp1, ura3 | | |
| AYE-1 | MATα YPH500 (pEAC6a) | Leu+, Ura+ | |
| AYE-2 | MATα YPH500 (pEAC8a) | Leu+, Ura+ | |
| AYE-3 | MATα YPH500 (pEAC9) | Leu+, Ura+ | |
| AY-2 | MATα YPH500 | Ura+ | EGFPuv - CWP2 (pUAC19a) |
| AY-5 | MATα YPH500 | Leu+, Ura+ | EGFPuv - CWP2 × 2(pUAC19a, pUAC20a) |
| AY-10 | MATα YPH500 | Leu+, Trp+ | EGFPuv - CWP2(pUAC20a, pUAC21a) |
| AY-12 | MATα YPH500 | Leu+, Ura+ | EGFPuv - GAS1 × 2(pUAC29b, pUAC31b) |
| AY-14 | MATα YPH500 | Leu+, Trp+, Ura+ | EGFPuv - CWP2 × 3 (pUAC19a, pUAC20a. pUAC21a) |
| AY-15 | MATα YPH500 | Leu+, Trp+, Ura+ | EGFPuv - GAS1 × 3 (pUAC29b, pUAC30b. pUAC31b) |
| AY-16 | MATα YPH500 kre6Δ::URA3 | Leu+, Trp+, Ura+ | EGFPuv - CWP2 × 2(pUAC20a. pUAC21a) |
| AY-17 | MATα YPH500 | Leu+, Ura+ | GFPuv - CWP2 × 2(pUAC19, pUAC20) | pEAC8a: A mutation was introduced into pEAC8 (primer: YEX-SM6).

pEAC9: A fragment obtained by digesting pUAC14 with SacI and BglII was inserted between the SacI and BglII sites of pEAC6a.

pEAC11: A fragment obtained by digesting pEAC7a with SacI and NdeI was inserted between the SacI and NdeI sites of pUAC16.

pEAC12: A fragment obtained by digesting pEAC9 with SacI and BglII was inserted into the SacI and BglII sites of pEAC11.

In FIG. 1, for pEAC6a, Reporter is α-galactosidase. For pEAC8a, Reporter is GFPuv. For pUAC19, Reporter is EGFP, Marker is URA3, and AS is CWP2 anchoring signal. For pUAC19a, Reporter is EGFP, Marker is URA3, and AS is CWP2 anchoring signal. For pUAC20a, Reporter is EGFP, Marker is LEU2, and AS is CWP2 anchoring signal. For pUAC21a, Reporter is EGFP, Marker is TRP1, and AS is CWP2 anchoring signal. For pUAC29b, Reporter is EGFP, Marker is LEU2, and AS is GAS1 anchoring signal. For pUAC30b, Reporter is EGFP, Marker is URA3, and AS is GAS1 anchoring signal. For pUAC31b, Reporter is EGFPuv, Marker is TRP1, and AS is GAS1 anchoring signal.

(E) Preparation of Arming Yeast

As a reporter protein, α-galactosidase derived from S. cerevisiae (Turakainen, H., et al., Appl. Environ. Microbiol., 59, 2622-2630, 1993; MEL1) or a green fluorescent protein (GFP) was chosen. As GFP, GFPuv and EGFPuv (Cormack, B. P., et al., Gene, 173, 33-38, 1996; obtained by introducing a mutation into GFPuv so that Phe64 and Ser65 is replaced with Leu and Thr, respectively) were used. A gene coding for a fusion protein which consists of each of the proteins added with a secretory signal of SUC2 at the N-terminus and a GPI anchoring signal of CWP2 at the C-terminus was designed, and the gene was inserted between the promoter and the terminator of phosphoglycerate kinase gene to obtain an expression cassette. Wall-type arming yeasts were obtained by transformation using a plasmid obtained by inserting the expression cassette into a YEp-type vector (pEAC6a, pEAC8a or pEAC9) for AYE1, AYE2 or AYE3 strain, or by (F) Media YPAUD (1% yeast extract, 2% peptone, 2% glucose, 40 μg/ml of adenine, 20 μg/ml of uracil), RPMIB (RPMI1640 (Sigma), 1 M sorbitol, 100 mM potassium phosphate buffer (pH 4.0-7.0), 2% glucose, 40 μg/ml of adenine, 20 μg/ml of uracil) and YNB (0.67% yeast nitrogen base without amino acid (Difco), 2% glucose, additional nutrients (40 μg/ml of adenine, 20 μg/ml of histidine, 60 μg/ml of leucine, 30 μg/ml of lysine, 40 μg/ml of tryptophan, 20 μg/ml of uracil)) were appropriately used. Agar media were obtained by adding 1.5-2% agarose to the aforementioned liquid media.

(G) Determination of α-galactosidase Activity

The method of Schreuder et al. (Schreuder, M. P., et al., Yeast, 9, 399-409, 1993) was used. 160 μl of a culture broth of a yeast strain cultured in YNB in the late logarithmic growth phase was added with 20 μl each of 1 M acetate buffer (pH 4.5) and 0.1 M p-nitrophenyl-α-galactopyranoside (Boehringer Manheim) and allowed to react at 37° C. for 5 minutes. The reaction mixture was added with 1 ml of 2% sodium carbonate, and then the absorbance ($OD_{410}$) was measured.

(H) Measurement of Fluorescence Intensity of GFP-Expressing Strain

Yeast cells cultured in RPMIB (pH 7.0) in the logarithmic growth phase were collected and resuspended with water at $OD_{595}$=1.0, and measurement was performed. The fluorescence intensity and the optimum wavelengths were measured by using a fluorometer (F-2000, Hitachi Koki Co., Ltd.). Further, fluorescence of each cell was detected by using a fluorescence microscope (Axioplan, Zeiss).

(I) Determination of GFP Releasing Effect by Zymolyase Action

Yeast cells cultured in a liquid medium in the logarithmic growth phase were collected and resuspended with an appropriate buffer. The mixture was added with 400-6.25 μg/ml of Zymolyase 100T (Seikagaku Corporation) and shaken at 30° C. for 30 minutes. After the reaction, the yeast cells and the buffer were separated by filtration through a filter, and fluorescence intensity in the buffer was measured by a fluorometer (excitation=487 nm, emission=513 nm).

(J) Comparison of GFP Localization

Yeast cells (AY-2 strain) cultured in a liquid medium in the logarithmic growth phase were physically disrupted by using glass beads, then the cell wall, cell membrane and soluble proteins were fractionated, and each fraction was suspended in an appropriate buffer. The fluorescence intensity of each fraction was measured (excitation=487 nm, emission=513 nm) and represented in terms of a ratio based on the total fluorescence intensity of the whole cells.

(K) Determination of GFP Releasing Effect in KRE6-Disrupted Strain

The KRE6-disrupted strain (AY-16 strain) was cultured with shaking at 30° C. The culture fluid was filtered using a filter after 3 and 6 hours, and fluorescence intensity in the medium was measured.

(L) Measurement of GFP Releasing Effect of Commercially Available Antifungal Agents The cultured yeast cells in the logarithmic growth phase (AY-2 strain or AY-12 strain) were collected, and various agents were allowed to act on the yeast cells. Fluorescence intensity of the culture supernatant was measured by using Cytofluor 2300 Fluorometer (Millipore, excitation=480 nm, emission=530 nm). The fluorescence intensity under treatment with each of various agents was shown in terms of a difference in fluorescence intensity compared with that of a control in which no agent was added.

(2) Results (A) Characterization of Various Wall-Type Arming Yeast

Various wall-type arming yeasts were produced by using three kinds of reporter proteins, α-galactocidase, GFPuv and EGFPuv, and applying a method of using a high copy number vector or a method of insertion into the chromosome as an expression method, and α-galactosidase activity and fluorescence intensity given by these yeast strains were compared. As a result, only weak activity was observed in both of the α-galactosidase-expressing strains (AYE-1 strain and AYE-2 strain). Further, when a yeast strain (AYE-3 strain) in which GFPuv was expressed by using a high copy number vector was examined with a fluorescence microscope, significant scattering was observed in the fluorescence intensity among individual cells, which suggested that there was a problem in stability of the plasmid. Whilst when fluorescence intensities of the strains obtained by inserting EGFPuv and GFPuv expression cassettes into the chromosome (AY-5 strain and AY-17 strain) were compared (Table 3), the fluorescence intensity of EGFPuv was three or more times stronger than that of GFPuv. Based on these results, it was concluded that use of a fluorescent protein as the reporter protein was appropriate and that the strain in which EGFPuv was inserted into the chromosome as the reporter protein was particularly preferred. When the optimum wavelengths of the strain were measured, excitation max was found as 487 nm, and emission max as 513 nm.

TABLE 3

|  | Excitation (nm) | Emission (nm) | Fluorescence |
| --- | --- | --- | --- |
| YPH500 | 487 | 513 | 260 |
| AY-5 | 487 | 513 | 1260 |
| YPH500 | 395 | 509 | 50 |
| AY-17 | 395 | 509 | 350 |

The strain in the logarithmic growth phase was suspended in water and its fluorescence intensity was measured.

(B) Measurement of GFP Releasing Effect by Zymolyase Action

The AY-2 strain was grown in a test tube, and the cells were collected and treated with Zymolyase. The fluorescence intensity in the culture supernatant after Zymolyase treatment. When Zymolyase was allowed to act on the AY-2 strain under osmotic pressure protection, the fluorescence intensity in the buffer increased depending on the concentration of the added Zymolyase (Table 4). These results suggested that a large amount of GFP was fixed on the cell wall.

TABLE 4

| Zymolyase (μg/ml) | Fluorescence intensity |
| --- | --- |
| 400 | 2160 |
| 200 | 1240 |
| 100 | 1170 |
| 50 | 786 |
| 25 | 410 |
| 12.5 | 215 |
| 6.25 | 126 |
| 0 | 107 |

(C) Measurement of GFP Releasing Effect in KRE6-Disrupted Strain

It is estimated that at least 6 kinds of enzymes are involved in the biosynthesis of (1,6)-β-glucan in *Saccharomyces cerevisiae*. Among these enzymes, it has been revealed that at least one of a product (a protein) encoded by the KRE6-gene present in the Golgi body and a product (a protein) encoded by SKN1 gene, which is a homologue thereof, is essential for the growth (Gaughran, J. P. et al., J. Bacteriol., 176, pp.5857-5860, 1994). Further, it is estimated that KRE6 homologues widely exist also in fungi such as *Candida albicans* (typical pathogenic fungus). Based on the above findings, Kre6p (a KRE6 gene product) is expected to be a preferred target for development of novel antifungal agents.

Figure 2:
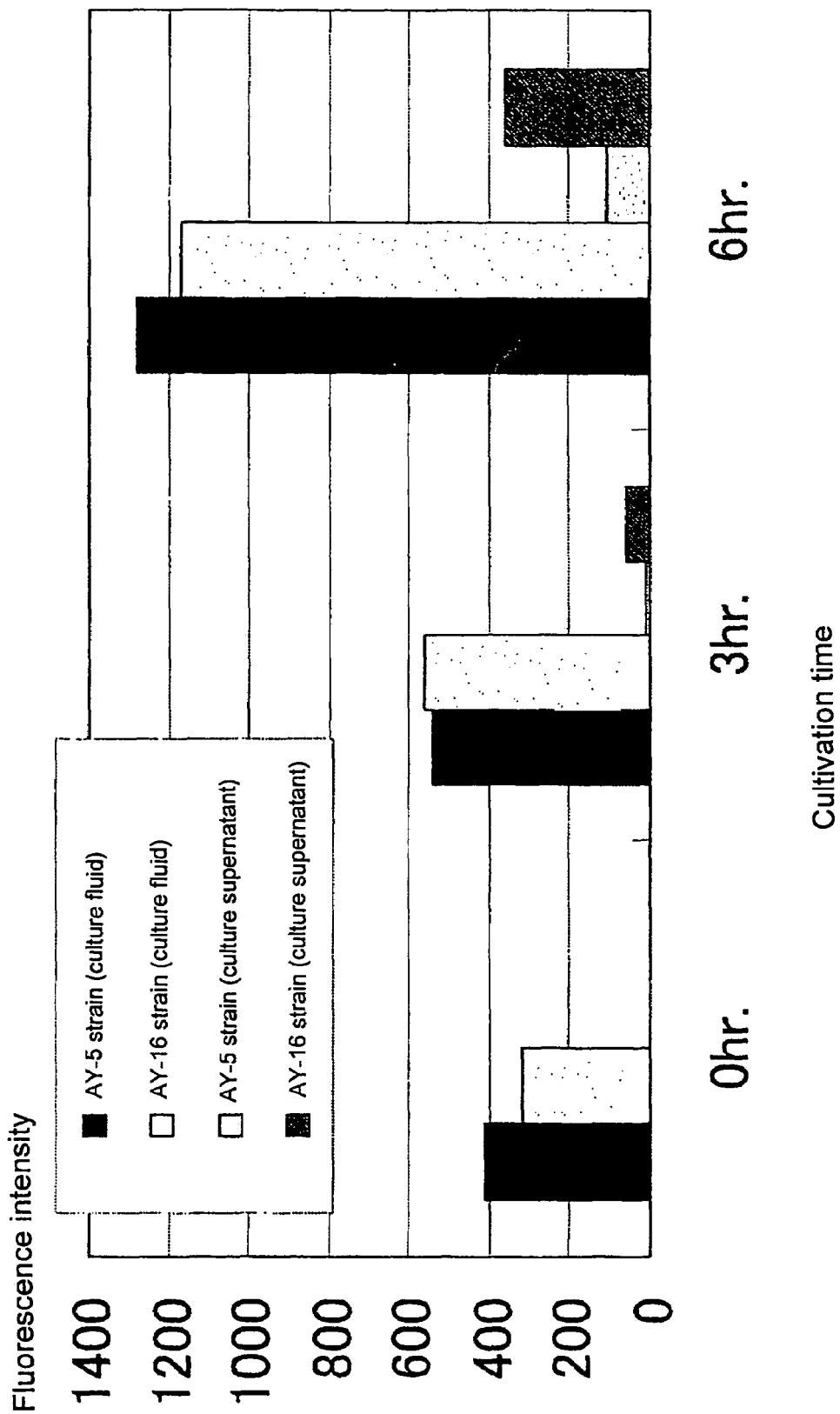
FIG. 2 shows results of time course measurement of GFP release based on fluorescence intensity in the culture fluid and the culture supernatants of the AY-5 strain and the AY-16 strain cultured in test tubes.

In order to verify the GFP releasing effect by the disruption of KRE6, the AY-5 strain and the AY-16 (KRE6-disrupted) strain were cultured in test tubes, and release of GFP with passage of time was measured (FIG. 2). As a result, almost same level of fluorescence intensities were detected in the culture fluids (yeast+medium) for the both strains at any time during the cultivation period, whilst the fluorescence intensity in the culture supernatant of the AY-16 strain was apparently higher than that of the AY-5 strain. Further, when these two yeast strains were cultured in test tubes and cells in the logarithmic growth phase were examined under a fluorescence microscope (×400), the fluorescence intensity of the AY-16 strain was attenuated. These results suggest that disruption of KRE6 accelerates GFP release. Accordingly, these experiment results indicate that an agent inhibiting the KRE6-gene product can be successfully screened by using the microorganisms prepared (arming yeasts).

(D) Comparison of GFP Localization

Localization of GFP was compared in the AY-2 strain (wall-type arming yeast) and the AY-12 strain (membrane-type arming yeast). Each yeast strain was grown in a test tube, and cells were collected and fractionated into cell wall, cell membrane, and soluble proteins. Fluorescence intensities of the resulting fractions were measured and each ratio on the basis of the total fluorescence intensity was calculated (unit: %). The results are shown in Table 5. It was revealed that a respective large amount of GFP was fixed on the cell wall of the wall-type arming yeast and the cell membrane of the membrane-type arming yeast.

TABLE 5

|  | AY-2 | AY-12 |
|---|---|---|
| Cell wall fraction | 40 | 11 |
| Cell membrane fraction | 15 | 48 |
| Soluble protein fraction | 45 | 41 |

(E) Measurement of GFP Releasing Effect of Available Antifungal Agents

Figure 3:
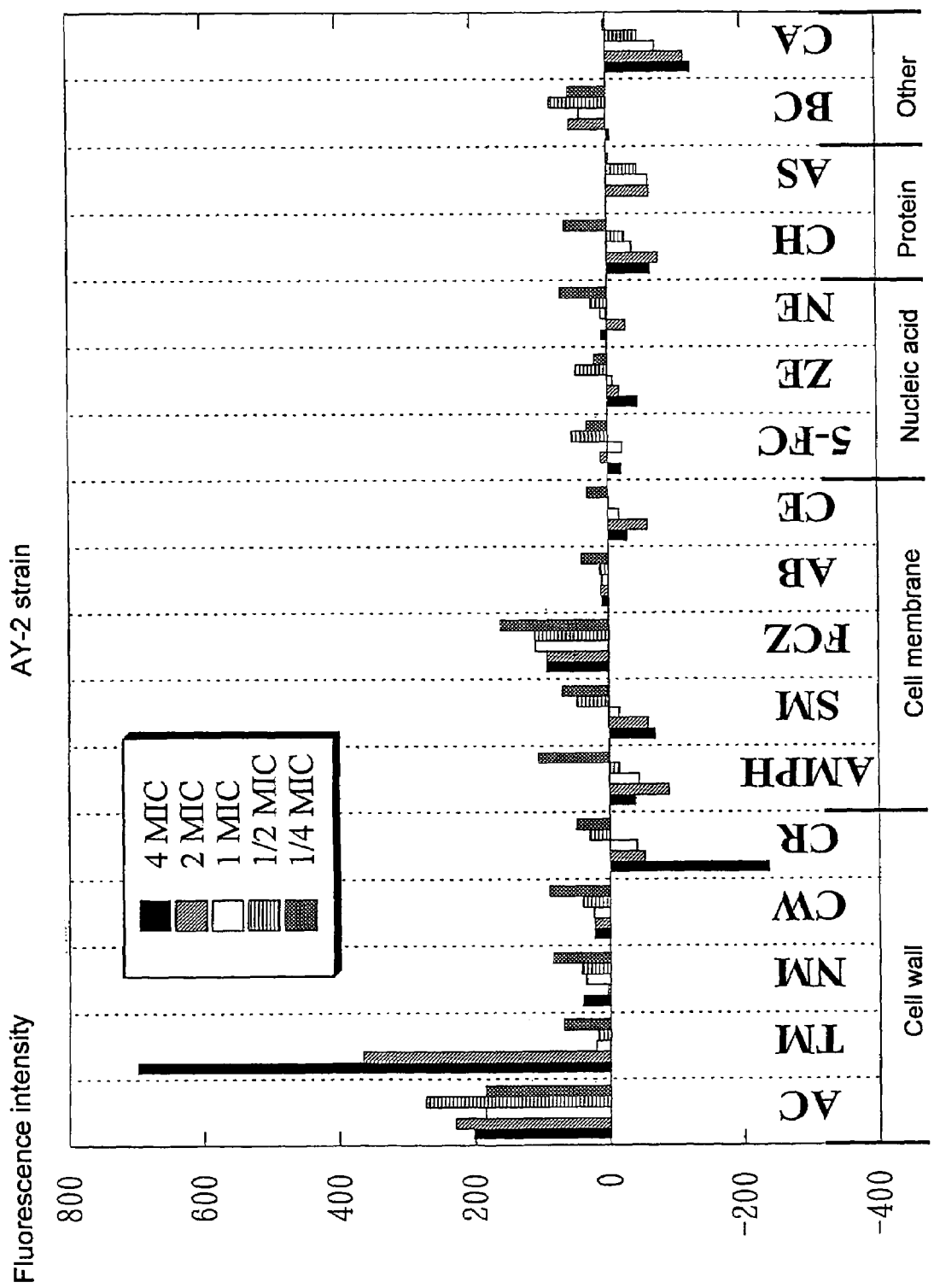
FIG. 3 shows GFP releasing effects by available antifungal reagents. Each macromolecule mainly inhibited is parenthesized. The upper graph shows the results obtained by use of the AY-2 strain, and the lower graph shows the results obtained by use of the AY-12 strain. Agents shown from the left are aculeacin A (AC), tunicamycin (TM), nikkomycin (NM), calcofluor white (CW), Congo red (CR), amphotericin B (AMPH), salinomycin (SM), fluconazole (FCZ), aureobasidin (AB), cerulenin (CE), 5-flucytosine (5-FC), zeocin (ZE), netropsin (NE), cycloheximide (CH), azaserine (AS), bromoconduritol (BC) and caffeine (CA).
Figure 3:
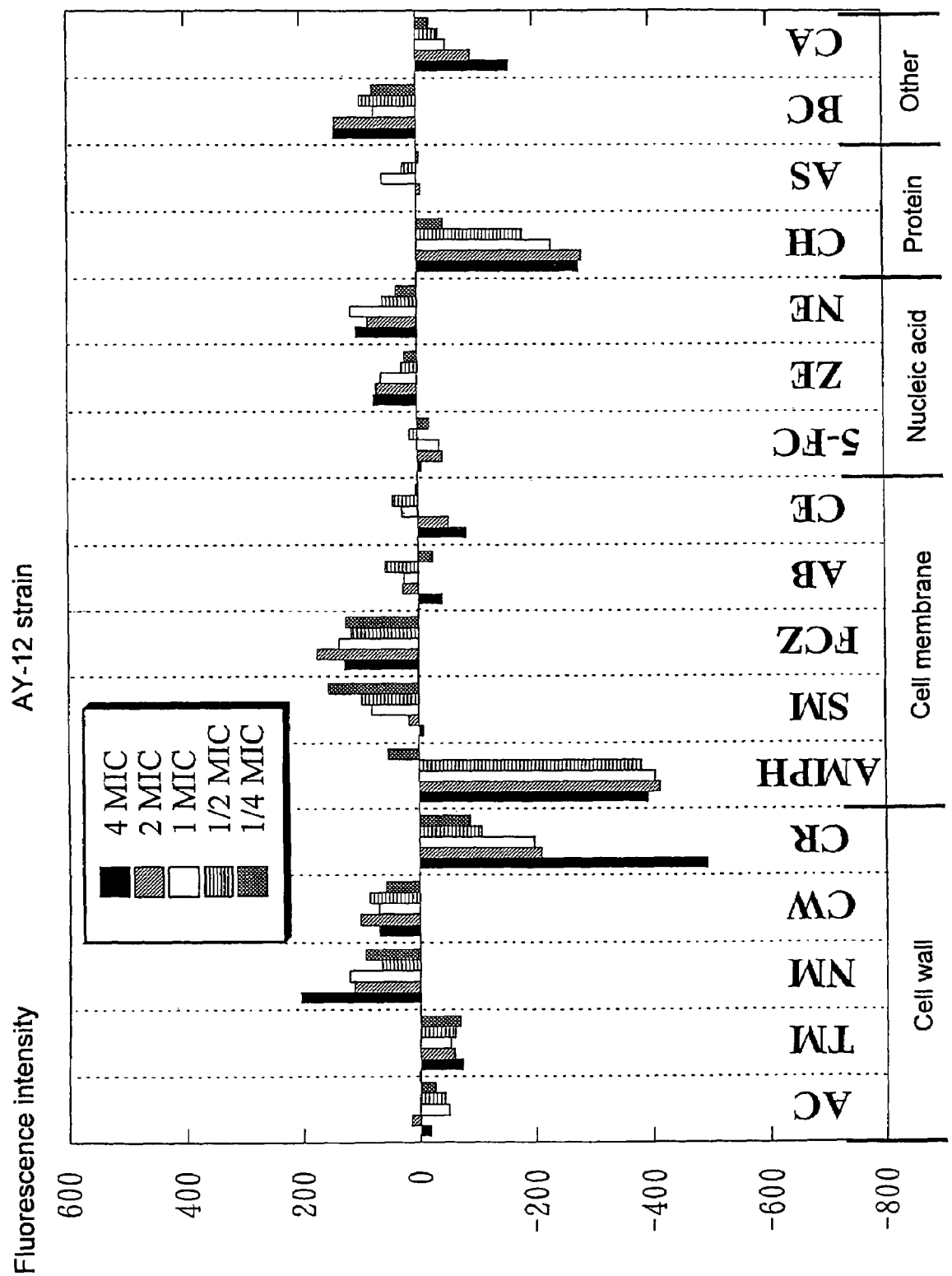

In order to ascertain whether or not the aforementioned method can be utilized for a screening of agents with a targeting site other than Kre6p, the GFP releasing effects in the AY-2 strain (wall-type arming yeast) and the AY-12 strain (membrane-type arming yeast) were compared under actions of available antifungal agents. The AY-2 strain cells and the AY-12 strain cells each cultured in a test tube were suspended with a medium (RPMIB) protected for osmotic pressure, and each of the agents was allowed to act on the cells. After the culture, the fluorescence intensity of the supernatant was measured, and a difference from that of a control with no addition of the agent was calculated. The results are shown in FIG. 3.

Marked GFP releasing effect was observed in the AY-2 strain treated with Aculeacin A ((1,3)-β-glucan synthesis inhibitor) and Tunicamycin (mannan synthesis inhibitor) both acting on cell walls, whereas almost no releasing effect was observed in the AY-12 strain. Slight releasing effect was observed in the both strains treated with Amphotericin B, Fluconazole and Salinomycin which act on cell membrane. Agents other than the above gave no clear GFP releasing effect only on the wall-type arming yeast (AY-2 strain). These results revealed that various kinds of agent acting on a cell wall can be successfully screened by the aforementioned screening method.

The genes incorporated in the microorganisms, the AY-15 strain and the AY-14 strain, are shown in the following Sequence Listing.

SEQ ID NO: 1 is the gene incorporated in the AY-15 strain, which is a membrane-type arming yeast, as a genome-incorporated type gene. The gene corresponds to a nucleotide sequence of SS (secretory signal)-EGFPuv-membrane anchoring signal (AS) and was obtained by adding mutations to a commercially available GFPuv (312th position was substituted with "g", 315th position with "a", and 316th position with "a" for the nucleotides in the original GFPuv being t, c and t, respectively).

SEQ ID NO: 2 is the gene incorporated in the AY-14 strain, which is a wall-type arming yeast, as a genome-incorporated type gene. The gene corresponds to a nucleotide sequence of SS (secretory signal)-EGFPuv-wall anchoring signal (AS) and was obtained by adding mutations to a commercially available GFPuv (312th position was replaced with "g", 315th position with "a" and 316th position with "a" for the nucleotides in the original GFPuv being t, c and t, respectively).

Example 2 (Present Invention)

(1) Test Materials and Methods (A) Strains, Cells, Transformation Method and Media

*Escherichia coli* strains JM109 and DH5α, and *Saccharomyces. cerevisiae* strains YPH499 and YPH500 were used. Transformation was performed according to the method described in Example 1 mentioned above or by using a yeast transformation kit (Invitrogen, Carlsbad, Calif., USA) according to the packaged manual. The strains used in this example are shown in Table 6. As for the medium, those described in Example 1 were appropriately used.

TABLE 6

| Strain | Genotype | Phenotype | Gene manipulation |
|---|---|---|---|
| YPH499 | MATa ade2, his3, leu2, lys2, trp1, ura3 | | |
| YPH500 | MATα ade2, his3, leu2, lys2, trp1, ura3 | | |
| AY-10 | MATα YPH500 | Leu+, Trp+ | EGFP-CWP2 × 2(pUAC20a, pUAC21a) |
| AY-10u | MATα YPH500 | Leu+, Trp+, Ura+ | EGFP-CWP2 × 2(pUAC20a, pUAC21a), pUXS1 |
| AY-10a | MATα YPH500 gas1::URA3 | Leu+, Trp+, Ura+ | EGFP-CWP2 × 2(pUAC20a, pUAC21a), pUAB6 |
| AY-10b | MATα YPH500 kex2::URA3 | Leu+, Trp+, Ura+ | EGFP-CWP2 × 2(pUAC20a, pUAC21a), pUAB8 |
| AY-10c | MATα YPH500 skn1::URA3 | Leu+, Trp+, Ura+ | EGFP-CWP2 × 2(pUAC20a, pUAC21a), pUAB10 |
| AY-10d | MATα YPH500 bck1::URA3 | Leu+, Trp+, Ura+ | EGFP-CWP2 × 2(pUAC20a, pUAC21a), pUAB18 |
| AY-10e | MATα YPH500 pmt1::URA3 | Leu+, Trp+, Ura+ | EGFP-CWP2 × 2(pUAC20a, pUAC21a), pUAB19 |
| AY-10f | MATα YPH500 pmt2::URA3 | Leu+, Trp+, Ura+ | EGFP-CWP2 × 2(pUAC20a, pUAC21a), pUAB20 |
| AY-10g | MATα YPH500 pmt4::URA3 | Leu+, Trp+, Ura+ | EGFP-CWP2 × 2(pUAC20a, pUAC21a), pUAB21 |
| AY-10h | MATα YPH500 fks1::URA3 | Leu+, Trp+, Ura+ | EGFP-CWP2 × 2(pUAC20a, pUAC21a), pUAB23 |
| AY-10i | MATα YPH500 kre2::URA3 | Leu+, Trp+, Ura+ | EGFP-CWP2 × 2(pUAC20a, pUAC21a), pUAB22 |
| AY-10j | MATα YPH500 | Leu+, Trp+, Ura+ | EGFP-CWP2 × 2(pUAC20a, pUAC21a), pUAB24 |
| AY-10k | MATa YPH500 kre6::URA3 | Leu+, Trp+, Ura+ | EGFP-CWP2 × 2(pUAC20a, pUAC21a), pUAB9 |
| AY-10l | MATα YPH500 gpi::URA3 | Leu+, Trp+, Ura+ | EGFP-CWP2 × 2(pUAC20a, pUAC21a), pUAB7 |
| AY-12 | MATα YPH500 | Leu+, Trp+ | |
| AY-12u | MATα YPH500 | Leu+, Trp+, Ura+ | EGFP-GAS1 × 2(pUAC20b, pUAC21b), pUXS1 |
| AY-12a | MATα YPH500 gas1::URA3 | Leu+, Trp+, Ura+ | EGFP-GAS1 × 2(pUAC20b, pUAC21b), pUAB6 |
| AY-12b | MATα YPH500 kex2::URA3 | Leu+, Trp+, Ura+ | EGFP-GAS1 × 2(pUAC20b, pUAC21b), pUAB8 |
| AY-12c | MATα YPH500 skn1::URA3 | Leu+, Trp+, Ura+ | EGFP-GAS1 × 2(pUAC20b, pUAC21b), pUAB10 |
| AY-12d | MATα YPH500 bck1::URA3 | Leu+, Trp+, Ura+ | EGFP-GAS1 × 2(pUAC20b, pUAC21b), pUAB18 |
| AY-12e | MATα YPH500 pmt1::URA3 | Leu+, Trp+, Ura+ | EGFP-GAS1 × 2(pUAC20b, pUAC21b), pUAB19 |
| AY-12f | MATα YPH500 pmt2::URA3 | Leu+, Trp+, Ura+ | EGFP-GAS1 × 2(pUAC20b, pUAC21b), pUAB20 |
| AY-12g | MATα YPH500 pmt4::URA3 | Leu+, Trp+, Ura+ | EGFP-GAS1 × 2(pUAC20b, pUAC21b), pUAB21 |
| AY-12h | MATα YPH500 fks1::URA3 | Leu+, Trp+, Ura+ | EGFP-GAS1 × 2(pUAC20b, pUAC21b), pUAB23 |
| AY-12i | MATα YPH500 kre2::URA3 | Leu+, Trp+, Ura+ | EGFP-GAS1 × 2(pUAC20b, pUAC21b), pUAB22 |
| AY-12j | MATα YPH500 | Leu+, Trp+, Ura+ | EGFP-GAS1 × 2(pUAC20b, pUAC21b), pUAB24 |
| AY-12k | MATα YPH500 kre6::URA3 | Leu+, Trp+, Ura+ | EGFP-GAS1 × 2(pUAC20b, pUAC21b), pUAB9 |
| AY-12l | MATα YPH500 gpi::URA3 | Leu+, Trp+, Ura+ | EGFP-GAS1 × 2(pUAC20b, pUAC21b), pUAB7 |

TABLE 6-continued

| Strain | Genotype | Phenotype | Gene manipulation |
|---|---|---|---|
| AY-14 | MATα YPH500 | Leu+, Trp+, Ura+ | EGFP-CWP2 × 3(pUAC19a, pUAC20a, pUAC21a) |
| AY-15 | MATα YPH500 | Leu+, Trp+, Ura+ | EGFP-GAS1 × 3(pUAC19b, pUAC20b, pUAC21b) |

(B) Oligonucleotides

The following 24 kinds of oligonucleotides were synthesized and appropriately used in the experiment.

```
                                         (SEQ ID NO: 27)
KRE6-Sen3
(5'-CGCGGCCGTAACAAAACGAACAACATGAGACAAAACCCG-3')

(SEQ ID NO: 28)
KRE6-Ant3
(5'-CGAGGCCTTTAGTTCCCTTTATGACCCGATTTGAAC-3')

(SEQ ID NO: 29)
SKN1-Sen1
(5'-CGAAGCTTCTTCGTATTTTCAGTCGCTC-3')

(SEQ ID NO: 30)
SKN1-Ant1
(5'-CGATGGCTGCTTCCGTACCCAAATCT-3')

(SEQ ID NO: 31)
GAS1-Sen1
(5'-GCGCATGCCGCAAACGTGGAGATGGGAA-3')

(SEQ ID NO: 32)
GAS1-Ant1
(5'-GCCCGCGGCTTATCGAGTTATTATGTATGTGTCGAAGC-3')

(SEQ ID NO: 33)
GPI1-Sen1
(5'-GCGCATGCTTCCTTATGTTAGCTTGTCACC-3')

(SEQ ID NO: 34)
GPI1-Ant1
(5'-GCGCATGCCTTTACACTCAATGGCTTACATGGCA-3')

(SEQ ID NO: 35)
KEX2-Sen1
(5'-GCGCATGCGACGTGTTCTTTCTCTCGTTTC-3')

(SEQ ID NO: 36)
KEX2-Ant1
(5'-GCGCATGCATTTTATTCGCGGGTGCAAACAAT-3')

(SEQ ID NO: 37)
BCK1-Sen1
(5'-GCGCATGCAGCACATACACATTCTAGGTCTGATTCG-3')

(SEQ ID NO: 38)
BCK1-Ant1
(5'-GCGCATGCGGAATTGGTGGTGCCGATTTTGACTTTCC-3')

(SEQ ID NO: 39)
PMT1-Sen1
(5'-GCGCATGCTCATTCTACGCTTGTCATCCAC-3')

(SEQ ID NO: 40)
PMT1-Ant1
(5'-GCGCATGCGCGAAATGATAATACCACTGAAACTACTTG-3')

(SEQ ID NO: 41)
PMT2-Sen1
(5'-GCCAGCTGGTTCTTTCCATATTCACCACGTTTGTCG-3')

(SEQ ID NO: 42)
PMT2-Ant1
(5'-GCCAGCTGAGTACCAGAAGCAACCAATTACAAGTGCCA-3')

(SEQ ID NO: 43)
PMT4-Sen1
(5'-GCGCATGCGTTGAAGTACACGAAGGCCGCGC-3')

(SEQ ID NO: 44)
PMT4-Ant1
(5'-GCGCATGCAAGGCGTTCAGTTCGTTTGTGGTTAGTG-3')

(SEQ ID NO: 45)
KRE2-Sen1
(5'-GCGGATCCACCAGCAACAAACCAATACAGACCA-3')

(SEQ ID NO: 46)
KRE2-Ant1
(5'-GCGGATCCGTTTCATTTGTTTTATCTCGGCTCG-3')

(SEQ ID NO: 47)
MNN9-Sen1
(5'-GCGGATCCAAAAAATCATCATCACATCACAGAACCG-3')

(SEQ ID NO: 48)
MNN9-Ant1
(5'-GCGGATCCAAGCGCATTGACTGGAGAAGGT-3')

(SEQ ID NO: 49)
FKS1-Sen1
(5'-GCGGATCCATGAAACTCTAATCCTACTATCGGCG-3')

(SEQ ID NO: 50)
FKS1-Ant1
(5'-GCGGATCCTGCTCCTCATACCTTAAACCGG-3')
```

(C) Plasmids

Figure 8:
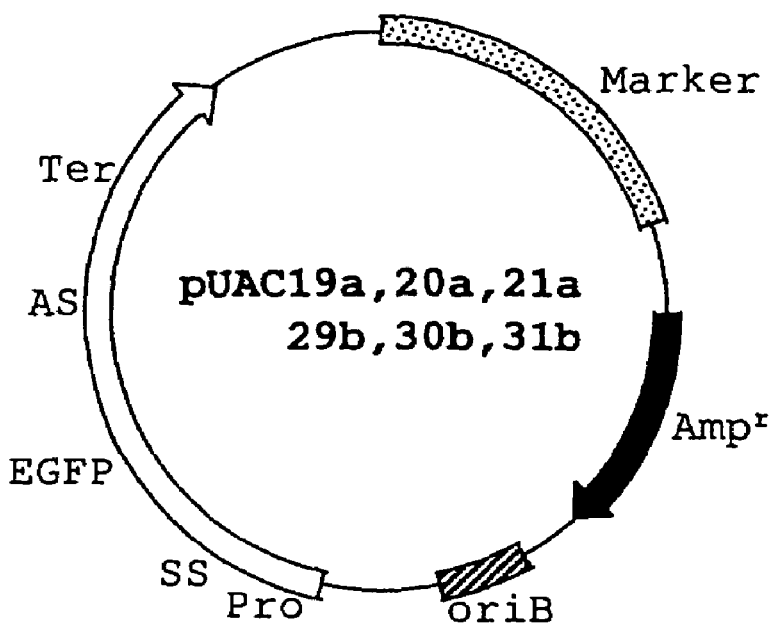
FIG. 8 shows the structures of plasmids pAUC19a, pUAC29b, pUAC20a, pUAC30b, pUAC21a, and pUAC31b used in the examples.

By using pAUC19a, pUAC29b, pUAC20a, pUAC30b, pUAC21a, pUAC31b (for these, see FIG. 8), pUC19 and YEp24 described in Example 1, the following plasmids were prepared. pGEM-T Vector System (Promega, Madison, Wis., USA) was used for subcloning of PCR products, and recovery of DNA fragments from agarose, ligation and digestion with restriction enzymes were performed according to the methods described in Example 1.

pUXS1: A fragment obtained by digesting YEp24 with HindIII (Ura3) was inserted into the HindIII site of pUC19.

pUAO1: KRE6 was amplified by PCR (template: YPH500 strain chromosomal DNA, primers: KRE6-sen3 and KRE6-ant3) and subcloned into pGEM-T.

pUAB1: SKN1 was amplified by PCR (template: YPH500 strain chromosomal DNA, primers: SKN1-sen1 and SKN1-ant1) and subcloned into pGEM-T.

pUAB3: GAS1 was amplified by PCR (template: YPH500 strain chromosomal DNA, primers: GAS1-sen1 and GAS1-ant1) and subcloned into PGEM-T.

pUAB4: GPI1 was amplified by PCR (template: YPH500 strain chromosomal DNA, primers: GPI1-sen1 and GPI1-ant1) and subcloned into pGEM-T.

pUAB5: KEX2 was amplified by PCR (template: YPH500 strain chromosomal DNA, primers: KEX2-sen1 and KEX2-ant1) and subcloned into pGEM-T.

pUAB6: A fragment obtained by digesting YEp24 with ClaI and SmaI was inserted into the ClaI and MscI sites of pUAB3.

pUAB7: A fragment obtained by digesting YEp24 with ClaI and SmaI was inserted into the ClaI and HpaI sites of pUAB4.

pUAB8: A fragment obtained by digesting YEp24 with ClaI and NheI was inserted into the ClaI and XbaI sites of pUAB5.

pUAB9: A fragment obtained by digesting YEp24 with BamHI and EcoRI was inserted into the BglII and EcoRI sites of pUAO1.

pUAB10: A fragment obtained by digesting pUXS1 with KpnI and PvuII was inserted into the ClaI and XbaI sites of pUAB1.

pUAB11: BCK1 was amplified by PCR (template: YPH500 strain chromosomal DNA, primers: BCK1-sen1 and BCK1-ant1) and subcloned into pGEM-T.

pUAB12: PMT1 was amplified by PCR (template: YPH500 strain chromosomal-DNA, primers: PMT1-sen1 and PMT1-ant1) and subcloned into pGEM-T.

pUAB13: PMT2 was amplified by PCR (template: YPH500 strain chromosomal DNA, primers: PMT2-sen1 and PMT2-ant1) and subcloned into pGEM-T.

pUAB14: PMT4 was amplified by PCR (template: YPH500 strain chromosomal DNA, primers: PMT4-sen1 and PMT4-ant1) and subcloned into pGEM-T.

pUAB15: KRE2 was amplified by PCR (template: YPH500 strain chromosomal DNA, primers: KRE2-sen1 and KRE2-ant1) and subcloned into pGEM-T.

pUAB16: FKS1 was amplified by PCR (template: YPH500 strain chromosomal DNA, primers: FKS1-sen1 and FKS1-ant1) and subcloned into pGEM-T.

pUAB17: MNN9 was amplified by PCR (template: YPH500 strain chromosomal DNA, primers: MNN9-sen1 and MNN9-ant1) and subcloned into pGEM-T.

pUAB18: A fragment obtained by digesting YEp24 with EcoRI and NheI was inserted into the EcoRI and NheI sites of pUAB11.

pUAB19: A fragment obtained by digesting YEp24 with EcoRI and SmaI was inserted into the EcoRI and EcoRV sites of pUAB12.

pUAB20: A fragment obtained by digesting YEp24 with EcoRI and SalI was inserted into the XhoI and MunI sites of pUAB13.

pUAB21: A fragment obtained by digesting YEp24 with ClaI and SmaI was inserted into the ClaI and HpaI sites of pUAB14.

pUAB22: A fragment obtained by digesting YEp24 with EcoRI and SmaI was inserted into the EcoRI and EcoRV sites of pUAB15.

pUAB23: A fragment obtained by digesting YEp24 with EcoRI and SmaI was inserted into the EcoRI and EcoRV sites of pUAB16.

pUAB24: A fragment obtained by digesting YEp24 with EcoRI and SmaI was inserted into the EcoRI and HpaI sites of pUAB17.

(D) Preparation of Arming Yeast and Gene-Disrupted Strains

Gene disruption was performed in a conventional manner. The prepared gene-disrupted strains are shown in Table 6 mentioned above together with the plasmids used. The AY-10k strain, AY-10l strain, AY-12k strain and AY-12l strain were prepared as follows. The YPH499 strain was transformed with YEp24, and the formed transformant was conjugated to the AY-10 strain or AY-12 strain. The plasmids were eliminated from the resulting diploids to obtain AY-17 strain and AY-18 strain, respectively. The AY-17 strain and AY-18 strain were transformed with an SphI digestion product of pUAB7 or Eco52I digestion product of pUAB9, and haploids were separated from the transformants obtained. The resulting haploids and the AY-10u strains were each inoculated to the RPMIB medium, and cultured at 30° C. with shaking. Fluorescence intensities of the resulting culture fluids were compared to select colonies exhibiting an intensity comparable to that obtained with the AY-10u strain as the AY-10k strain, AY-10l strain, AY-12k strain and AY-12l strain.

(E) GFP Releasing of Gene-Disrupted Strains and Comparison of Molecular Weights of Released GFP Cells at the logarithmic growth phase were collected after inoculation to the liquid medium and culture at 30° C., and suspended in a fresh medium of the same type to prepare a cell suspension for inoculation. The cells were cultured at 30° C. Fluorescence intensity of the culture supernatant was measured (excitation=480 nm, emission=530 nm) by using ARVO sx (Wallac, Tokyo). The GFP releasing effect of the gene-disrupted strains was represented in terms of a difference with that of a non-gene-disrupted strain (AY-10u strain or AY12u strain). After the measurement of fluorescence intensity, the culture supernatants were concentrated by ultrafiltration. The concentrated supernatants were subjected to separation by SDS-PAGE and blotted on a PVDF membrane, and GFP was detected by using commercially available anti-GFP antibodies (rabbit IgG, Santa Cruz Biotechnology) to compare the molecular weights (Western blotting).

(F) Change of GFP Molecular Weight Caused by Agent

As agents confirmed to have a yeast cell wall synthesis inhibitory action, tunicamycin (TM, Funakoshi, Tokyo), aculeacin A (AC, Wako Pure Chemical Industries, Osaka) and staurosporine (SP, Boehringer Mannheim, Tokyo) were used. The AY-14 strain was used as a microorganism.

(2) Results (A) Promotion of GFP-Release by Gene Disruption

Figure 9:
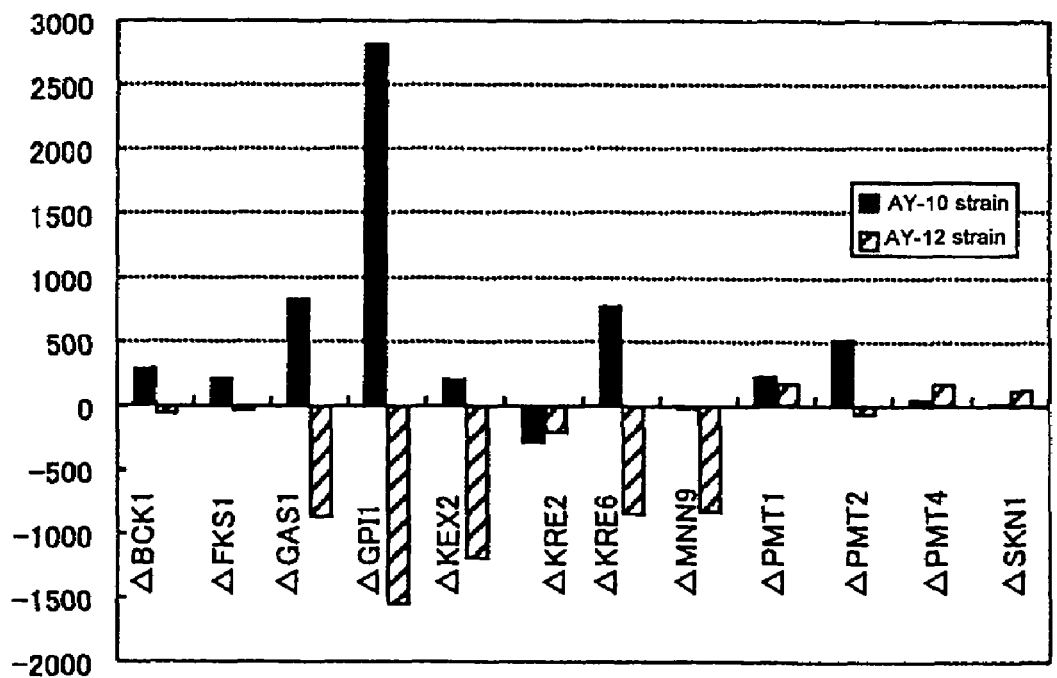
FIG. 9 shows the amounts of GFP released from a strain derived from the AY-12 strain (membrane-type arming yeast) as a parent strain wherein a cell wall synthesis gene is disrupted, and a strain derived from the AY-10 strain (wall-type arming yeast) as a parent strain wherein a cell wall synthesis gene is disrupted.

When synthesis of cell wall saccharide chains or normal cell wall synthesis is inhibited, GFP is released from cell walls into medium (Example 1). As shown in FIG. 9, when a gene involved in the cell wall synthesis (see Table 7) was disrupted, significant release was not observed for all of the gene-disrupted strains obtained from the AY-12 strain (membrane-type arming yeast) as a parent strain, whereas evident GFP release was observed for the gene-disrupted strains obtained from the AY-10 strain (wall-type arming yeast) as a parent strain, especially, the ΔGAS1 strain (Δ indicates disruption of the gene, and the same symbol will be used below), ΔGPI1 strain, ΔKRE6 strain and ΔPMT2 strain. These results suggest that agents inhibiting the (1,6)-β-glucan biosynthesis pathway (KRE6), biosynthesis of GPI-anchor (GPI1), synthesis pathway of O-type saccharide chains (PMT2) and hetero saccharide chain crosslinking reaction (GAS1) can be screened by this method.

TABLE 7

| Gene | Estimated or established function | Estimated Intracellular Localization | Enzyme specific to fungi | Reference |
|---|---|---|---|---|
| PMT1 | Synthesis of O-type saccharide chain | Rough endoplasmic reticulum | Yes | 16 |
| PMT2 | | | | |
| PMT4 | | | | |
| KRE2 | | Golgi body | No | 17 |
| MNN9 | Synthesis of N-type saccharide chain | Golgi body | No | 18 |
| FKS1 | Biosynthesis of (1,3)-β-glucan | Plasma membrane | Yes | 19 |
| KRE6 | Biosynthesis of (1,6)-β-glucan | Golgi body | Yes | 6 |
| SKN1 | | | | |

TABLE 7-continued

| Gene | Estimated or established function | Estimated Intracellular Localization | Enzyme specific to fungi | Reference |
|---|---|---|---|---|
| GPI1 | Synthesis of GPI-anchor | Rough endoplasmic reticulum | No | 20 |
| GAS1 | Crosslinking between glucan chains? | Plasma membrane | Yes | 21 |
| BCK1 | Synthesis of saccharide chains and synthesis of cell walls | Inside of cell | No | 3 |
| KEX2 | Processing of proteins | Golgi body | No | 22 |

16 Gentzsch, M. et al., EMBO J., 15, pp. 5752-5759, 1966
17 Hausler, A. et. al., Proc. Natl. Acad. Sci., 89, pp. 6846-6850, 1992
18 Dean, N., Biochim. Biophys. Acta., 1426, pp. 309-322, 1999
19 Mazur, P. et. al., Mol. Cell. Biol., 15, pp. 5671-5681, 1995
6 Romer, T. et al., Mol. Cell. Biol., 13, pp. 4039-4048, 1993
20 Leidich, S. D. et al., J. Biol. Chem., 269, pp. 10193-10196, 1994
21 Popolo, L., M. et. al., 1993 J. Bacteriol., 175, pp. 1879-1885, 1993
3 Cid, V. J. et. al. Microbiol. Rev., 59, pp. 345-386, 1995
22 Redding, K. et al., J. Cell. Biol., 113, pp. 527-538, 1991

When each of SP (PKC1 protein kinase C inhibitor), AC ((1,3)-β-glucan synthesis inhibitor) and TM (N-type saccharide chain synthesis inhibitor), which inhibit the synthesis of cell wall polymers, alone was allowed to act on the AY-14 strain in the experiment, release of GFP was observed (the releasing effects of AC and TM are as shown in Example 1). Thus, it is evident that inhibitors for the (1,3)-β-glucan synthesis pathway, N-type saccharide chain synthesis pathway, saccharide chain (glucan) synthesis regulatory pathway and the like can also be screened.

Among inhibition pathways (targeting sites) of the agent selected by this method, those suggested as pathways in which an enzyme specific to fungi exists and which exist only in fungi are the synthesis pathway of (1,3)-β-glucan, synthesis pathway of (1,6)-β-glucan, synthesis pathway of O-type saccharide chain and polymerization (or crosslinking) reaction of hetero saccharide chains (Table 7). Therefore, an operation is required to further choose agents inhibiting pathways or biochemical reactions specific to fungi for each targeting site from the agents selected by the aforementioned screening.

(B) Observation of Molecular Weight of GFP Released from Gene-Disrupted Strains

Figure 10:
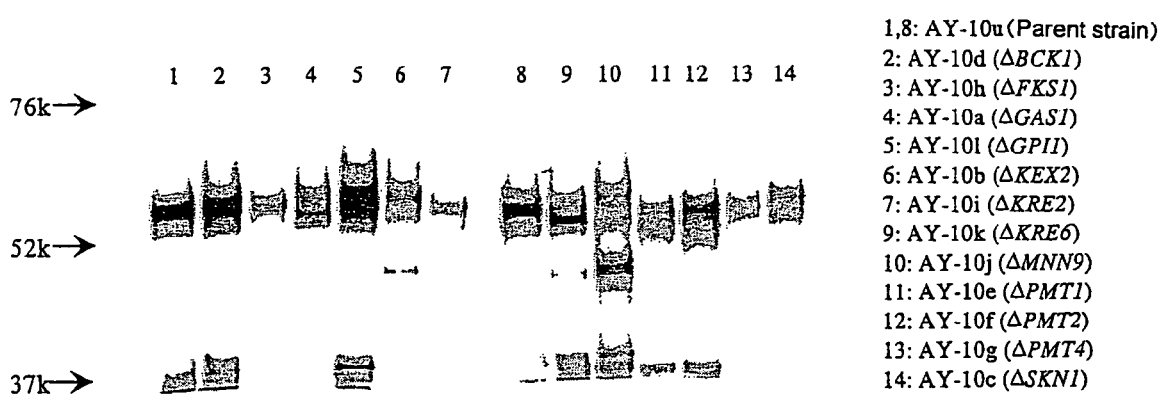
FIG. 10 shows results of the analysis of the molecular weights of GFP released from the gene-disrupted strains by Western blotting.

In FIG. 10, the results for analysis of molecular weight of GFP released from the gene-disrupted strains based on Western blotting are shown. As seen from these results, the molecular weight of GFP released from the gene-disrupted strains gave variety of changes.

Figure 11:
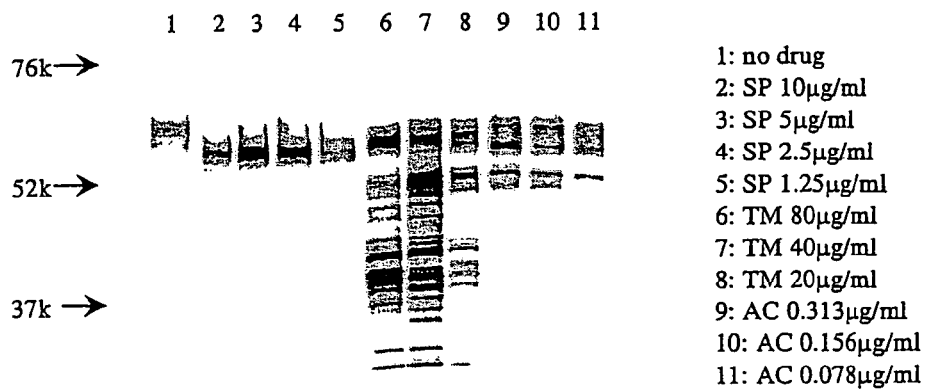
FIG. 11 shows results of comparison of the molecular weights of GFP released from the AY-14 strain after a treatment with each of SP (PKC1 protein kinase C inhibitor), AC ((1,3)-β-glucan synthesis inhibitor) and TM (N-type saccharide chain synthesis inhibitor) alone.

(C) Observation of Molecular Weight of GFP Released by Agent Inhibiting Cell Wall Synthesis In FIG. 11, shown are the results of comparison of molecular weights of released GFP observed when each of SP (PKC1 protein kinase C inhibitor), AC ((1,3)-β-glucan synthesis inhibitor) and TM (N-type saccharide chain synthesis inhibitor) alone was allowed to act on the AY-14 strain. The molecular weight of GFP was markedly lowered by the action of TM compared with that observed in the absence of the action of agent. Further, the molecular weight of released GFP was increased by about 10 kDa or less by the action of AC, whereas the molecular weight was lowered by about 10 kDa or less by the action of SP.

As already described, the presence of an enzyme specific to fungi is suggested in the synthesis pathway of (1,3)-β-glucan, synthesis pathway of (1,6)-β-glucan, synthesis pathway of O-type saccharide chain and polymerization (or crosslinking) reaction of hetero saccharide chains. When agents inhibiting any of these synthesis pathways or biochemical reaction were applied, the change of molecular weight of GFP was as small as within 10 kDa. By the screening of agents that provide such change in a molecular weight, agents that have selective action on fungi, especially on the cell walls of fungi, can be chosen.

Industrial Applicability

According to the method of the present invention, a targeting site of an agent having a selective inhibitory action on a cell wall can be conveniently and suitably determined, and thus an agent directed to a desired targeting site can be efficiently screened among from agents acting on a cell wall.

What is claimed is:

1. A method for screening an agent acting on a cell wall, which comprises the steps of:
   (1) culturing a microorganism having a reporter protein fixed on a cell wall as a GPI-anchored protein in the presence of a test agent acting on a cell wall;
   (2) analyzing a saccharide chain of a substance derived from the reporter protein released in a culture fluid of the microorganism; and
   (3) determining if the test agent has a selective inhibitory action on the cell wall on the basis of saccharide chain characteristics of the substance derived from the reporter protein obtained in step (2).

2. The method according to claim 1, which is used for screening of an agent directed to a particular targeting site from agents acting on a cell wall.

3. The method according to claim 1, wherein the analysis of the saccharide chain of the substance derived from the reporter protein is performed by measuring molecular weight of the substance derived from the reporter protein.

4. The method according to claim 1, wherein the reporter protein is a green fluorescent protein.

5. The method according to claim 1, wherein the agent acting on the cell wall is an antifungal agent.

6. The method according to claim 1, wherein, prior to the step (1), agents acting on a cell wall are screened by the following steps of:
   (A1) culturing each of a microorganism having a reporter protein fixed on a cell wall as a GPI-anchored protein and a microorganism having a reporter protein fixed on a cell membrane as a GPI-anchored protein in the presence of a test agent;
   (A2) determining a substance derived from the reporter protein released into each culture fluid of the microorganism cultured; and
   (A3) judging that the test agent is an agent having a selective inhibitory action on a cell wall when the substance derived from the reporter protein is released from the microorganism having the reporter protein fixed on the cell wall into the culture fluid and the substance derived from the reporter protein is not substantially released from the microorganism having the reporter protein fixed on the cell membrane into the culture fluid; and then the steps (1) to (3) are performed for agents determined to be agents having a selective inhibitory action on a cell wall in the step (A3).

7. A method for estimating a targeting site of an agent acting on a cell wall, which comprises the steps of:
   (1) culturing a microorganism having a reporter protein fixed on a cell wall as a GPI-anchored protein in the presence of a test agent acting on a cell wall;
   (2) analyzing a saccharide chain of a substance derived from the reporter protein released in a culture fluid of the microorganism; and
   (3) estimating a targeting site of the test agent on the cell wall on the basis of information of the saccharide chain of the substance derived from the reporter protein obtained in the step (2).

8. The method according to claim 2, wherein the analysis of the saccharide chain of the substance derived from the reporter protein is performed by measuring molecular weight of the substance derived from the reporter protein.

9. The method according to claim 2, wherein the reporter protein is a green fluorescent protein.

10. The method according to claim 3, wherein the reporter protein is a green fluorescent protein.

11. The method according to claim 2, wherein the agent acting on the cell wall is an antifungal agent.

12. The method according to claim 3, wherein the agent acting on the cell wall is an antifungal agent.

13. The method according to claim 4, wherein the agent acting on the cell wall is an antifungal agent.

14. The method according to claim 2, wherein, prior to the step (1), agents acting on a cell wall are screened by the following steps of:
   (A1) culturing each of a microorganism having a reporter protein fixed on a cell wall as a GPI-anchored protein and a microorganism having a reporter protein fixed on a cell membrane as a GPI-anchored protein in the presence of a test agent;
   (A2) determining a substance derived from the reporter protein released into each culture fluid of the microorganism cultured; and
   (A3) judging that the test agent is an agent having a selective inhibitory action on a cell wall when the substance derived from the reporter protein is released from the microorganism having the reporter protein fixed on the cell wall into the culture fluid and the substance derived from the reporter protein is not substantially released from the microorganism having the reporter protein fixed on the cell membrane into the culture fluid; and then the steps (1) to (3) are performed for agents determined to be agents having a selective inhibitory action on a cell wall in the step (A3).

15. The method according to claim 3, wherein, prior to the step (1), agents acting on a cell wall are screened by the following steps of:
   (A1) culturing each of a microorganism having a reporter protein fixed on a cell wall as a GPI-anchored protein and a microorganism having a reporter protein fixed on a cell membrane as a GPI-anchored protein in the presence of a test agent;
   (A2) determining a substance derived from the reporter protein released into each culture fluid of the microorganism cultured; and
   (A3) judging that the test agent is an agent having a selective inhibitory action on a cell wall when the substance derived from the reporter protein is released from the microorganism having the reporter protein fixed on the cell wall into the culture fluid and the substance derived from the reporter protein is not substantially released from the microorganism having the reporter protein fixed on the cell membrane into the culture fluid; and then the steps (1) to (3) are performed for agents determined to be agents having a selective inhibitory action on a cell wall in the step (A3).

16. The method according to claim 4, wherein, prior to the step (1), agents acting on a cell wall are screened by the following steps of:
   (A1) culturing each of a microorganism having a reporter protein fixed on a cell wall as a GPI-anchored protein and a microorganism having a reporter protein fixed on a cell membrane as a GPI-anchored protein in the presence of a test agent;
   (A2) determining a substance derived from the reporter protein released into each culture fluid of the microorganism cultured; and
   (A3) judging that the test agent is an agent having a selective inhibitory action on a cell wall when the substance derived from the reporter protein is released from the microorganism having the reporter protein fixed on the cell wall into the culture fluid and the substance derived from the reporter protein is not substantially released from the microorganism having the reporter protein fixed on the cell membrane into the culture fluid; and then the steps (1) to (3) are performed for agents determined to be agents having a selective inhibitory action on a cell wall in the step (A3).

17. The method according to claim 5, wherein, prior to the step (1), agents acting on a cell wall are screened by the following steps of:

(A1) culturing each of a microorganism having a reporter protein fixed on a cell wall as a GPI-anchored protein and a microorganism having a reporter protein fixed on a cell membrane as a GPI-anchored protein in the presence of a test agent;

(A2) determining a substance derived from the reporter protein released into each culture fluid of the microorganism cultured; and (A3) judging that the test agent is an agent having a selective inhibitory action on a cell wall when the substance derived from the reporter protein is released from the microorganism having the reporter protein fixed on the cell wall into the culture fluid and the substance derived from the reporter protein is not substantially released from the microorganism having the reporter protein fixed on the cell membrane into the culture fluid; and then the steps (1) to (3) are performed for agents determined to be agents having a selective inhibitory action on a cell wall in the step (A3).

* * * * *

SEQUENCE LISTING

<160> NUMBER OF SEQ ID NOS: 2

<210> SEQ ID NO 1
<211> LENGTH: 1116
<212> TYPE: DNA
<213> ORGANISM: Saccharomyces cerevisiae

<400> SEQUENCE: 1

```
actagtatgc ttttgcaagc tttccttttc cttttggctg gttttgcagc caaaatatct        60
gcatcaaaga gctcgcatgc ctgcaggtcg actctagagg atccccgggt accggtagaa       120
aaaatgagta aaggagaaga acttttcact ggagttgtcc caattcttgt tgaattagat       180
ggtgatgtta atgggcacaa attttctgtc agtggagagg gtgaaggtga tgcaacatac       240
ggaaaactta cccttaaatt tatttgcact actggaaaac tacctgttcc atggccaaca       300
cttgtcacta cgttaactta tggtgttcaa tgcttttccc gttatccgga tcatatgaaa       360
cggcatgact ttttcaagag tgccatgccc gaaggttatg tacaggaacg cactatatct       420
```

```
ttcaaagatg acgggaacta caagacgcgt gctgaagtca agtttgaagg tgatacccct    480
gttaatcgta tcgagttaaa aggtattgat tttaagaag atggaaacat tctcggacac    540
aaactcgagt acaactataa ctcacacaat gtatacatca cggcagacaa acaaaagaat    600
ggaatcaaag ctaacttcaa aattcgccac aacattgaag atggatccgt tcaactagca    660
gaccattatc aacaaaatac tccaattggc gatggccctg tccttttacc agacaaccat    720
tacctgtcga cacaatctgc cctttcgaaa gatcccaacg aaaagcgtga ccacatggtc    780
cttcttgagt ttgtaactgc tgctgggatt acacatggca tggatgagat ctgtagtgtt    840
gatttgggtt ccggaactga atccagtact gcctcttcta acgcttcggg gtcttcttcc    900
aagtctaact ccggctcttc tggttcttcc agttcttctt cttcttcttc agcttcatct    960
tcatcttcta gcaagaagaa tgctgccacc aacgttaaag ctaacttagc acaagtggtc   1020
tttacctcca tcatttcctt atccattgcc gctggtgtcg gttttgcttt ggtttaaaaa   1080
gcttcgacac atacataata actcgataag ccgcgg                             1116
```

<210> SEQ ID NO 2  
<211> LENGTH: 1236  
<212> TYPE: DNA  
<213> ORGANISM: Saccharomyces cerevisiae

<400> SEQUENCE: 2

```
actagtatgc ttttgcaagc tttccttttc cttttggctg gttttgcagc caaaatatct     60
gcatcaaaga gctcgcatgc ctgcaggtcg actctagagg atccccgggt accggtagaa    120
aaaatgagta aggagaagaa actttttcact ggagttgtcc caattcttgt tgaattagat    180
ggtgatgtta atgggcacaa atttctgtc agtggagagg gtgaaggtga tgcaacatac    240
ggaaaactta cccttaaatt tatttgcact actggaaaac tacctgttcc atggccaaca    300
cttgtcacta cgttaactta tggtgttcaa tgcttttccc gttatccgga tcatatgaaa    360
cggcatgact ttttcaagag tgccatgccc gaaggttatg tacaggaacg cactatatct    420
ttcaaagatg acgggaacta caagacgcgt gctgaagtca agtttgaagg tgatacccct    480
gttaatcgta tcgagttaaa aggtattgat tttaagaag atggaaacat tctcggacac    540
aaactcgagt acaactataa ctcacacaat gtatacatca cggcagacaa acaaaagaat    600
ggaatcaaag ctaacttcaa aattcgccac aacattgaag atggatccgt tcaactagca    660
gaccattatc aacaaaatac tccaattggc gatggccctg tccttttacc agacaaccat    720
tacctgtcga cacaatctgc cctttcgaaa gatcccaacg aaaagcgtga ccacatggtc    780
cttcttgagt ttgtaactgc tgctgggatt acacatggca tggatgagat ctctgaatcc    840
gctgccgcca tttctcaaat cactgacggt caaatccaag ctactaccac tgctaccacc    900
gaagctacca ccactgctgc cccatcttcc accgttgaaa ctgtttctcc atccagcacc    960
gaaactatct ctcaacaaac tgaaaatggt gctgctaagg ccgctgtcgg tatgggtgcc   1020
ggtgctctag ctgctgctgc tatgttgtta taagaaatct ctgattttt ataatatcta   1080 tatggctttt tcaaaattt tcggttttac taggtaagtg tttgattctt tcttttcgt   1140 taatatattt ttacacataa ttttaaataa ttttgttat tttgaatagg tagataccat   1200
aaaaataaaa cactttttac tttaacgagt ccgcgg                             1236
```